United States Patent [19]

Heiman et al.

[11] Patent Number: 5,262,333
[45] Date of Patent: Nov. 16, 1993

[54] METHOD AND REAGENTS FOR DETECTING AMPHETAMINE AND/OR D-METHAMPHETAMINE IN BIOLOGICAL SAMPLES

[75] Inventors: Daniel F. Heiman, Libertyville, Ill.; Sharon A. Johnson, Kenosha, Wis.; Hsiang-Yun Y. Hu, Libertyville, Ill.

[73] Assignee: Abbott Laboratories, Abbott Park, Ill.

[21] Appl. No.: 898,238

[22] Filed: Jun. 12, 1992

Related U.S. Application Data

[63] Continuation of Ser. No. 265,361, Oct. 28, 1988, abandoned.

[51] Int. Cl.$^5$ .......................................... G01N 33/542
[52] U.S. Cl. .................................... 436/537; 436/536; 436/546; 436/816
[58] Field of Search ............... 436/536, 537, 546, 816

[56] References Cited

U.S. PATENT DOCUMENTS

| | | | |
|---|---|---|---|
| 3,690,834 | 9/1972 | Goldstein et al. | 23/230 B |
| 3,704,282 | 11/1972 | Spector | 260/78 |
| 3,856,469 | 12/1974 | Schneider et al. | 23/230 B |
| 3,878,187 | 4/1975 | Schneider et al. | 424/88 |
| 3,940,475 | 2/1976 | Gross | 424/1 |
| 3,966,764 | 6/1976 | Goldstein et al. | 424/9 |
| 3,996,344 | 12/1976 | Gross | 424/88 |
| 4,016,146 | 4/1977 | Soares | 424/88 |
| 4,022,878 | 5/1977 | Gross | 424/1.5 |
| 4,041,076 | 8/1977 | Avenia et al. | 260/559 A |
| 4,067,774 | 1/1978 | Rubenstein et al. | 195/63 |
| 4,097,586 | 6/1978 | Gross | 424/1 |
| 4,122,078 | 10/1978 | Yoshioka et al. | 424/88 |
| 4,255,329 | 3/1981 | Ullman | 260/239 |
| 4,329,281 | 5/1982 | Christenson et al. | 424/88 |
| 4,351,760 | 9/1982 | Khanna et al. | 260/112 R |
| 4,420,568 | 12/1983 | Wang et al. | 436/536 |
| 4,476,228 | 10/1984 | Huckzermeier et al. | 436/500 |
| 4,476,229 | 10/1984 | Fino et al. | 436/500 |
| 4,481,136 | 11/1984 | Khanna et al. | 260/112 R |
| 4,492,762 | 1/1985 | Wang et al. | 436/537 |
| 4,510,251 | 4/1985 | Kirkemo et al. | 436/536 |
| 4,585,862 | 4/1986 | Wang et al. | 544/319 |
| 4,588,697 | 5/1986 | Khanna et al. | 436/518 |
| 4,593,089 | 6/1986 | Wang et al. | 536/13.6 |
| 4,681,859 | 7/1987 | Kramer | 436/501 |
| 4,751,190 | 6/1988 | Chiapetta et al. | 436/546 |
| 4,817,837 | 6/1974 | Rubenstein et al. | 195/103.5 R |
| 4,868,132 | 9/1989 | Byrnes et al. | 436/546 |
| 4,939,264 | 7/1990 | Heiman et al. | 436/825 |

FOREIGN PATENT DOCUMENTS

| | | |
|---|---|---|
| 0199042 | 10/1986 | European Pat. Off. |
| 0201751 | 11/1986 | European Pat. Off. |
| 0218010 | 4/1987 | European Pat. Off. |
| 0240021 | 10/1987 | European Pat. Off. |
| 0254120 | 4/1988 | European Pat. Off. |
| 0279213 | 8/1988 | European Pat. Off. |

(List continued on next page.)

OTHER PUBLICATIONS

"An Improved Label for Amphetamine Fluoroimmunoassay," Therapeutic Drug Monitoring 11:607–611 (1989).

(List continued on next page.)

Primary Examiner—Mary E. Ceperley
Attorney, Agent, or Firm—Gregory W. Steele; Thomas M. Breininger

[57] ABSTRACT

This disclosure relates to a method and reagents for determining amphetamine and d-methamphetamine in a biological fluid, such as urine. In particular, this disclosure relates to improvements in a fluorescence polarization immunoassay procedure for determining the presence of amphetamine and d-methamphetamine in a single assay and to a novel class of tracer compounds employed as reagents in such procedures. The procedure described includes pretreatment of the biological sample to eliminate cross reactants such as β-hydroxyphenethylamine by preincubating the sample solely with an aqueous periodate solution having a pH from about 4.0 to about 7.5 without adjustment to an alkaline pH, and contacting the sample with riboflavin binding protein to reduce interference from fluorescent components in the sample. The procedure also maintains the cross reactivity of the immunoassay for tyramine at about 0.4% and for l-methamphetamine below about 5.1% and eliminates the necessity of using controlled substances as starting materials.

17 Claims, No Drawings

FOREIGN PATENT DOCUMENTS 56-125666  2/1981  Japan .
2111476A  7/1983  United Kingdom ............... 436/546

OTHER PUBLICATIONS

Shipchandler, M. T., et al., "4'-[Aminomethyl]fluorescein and Its N-Alkyl Derivatives: Useful Reagents in Immunodiagnostic Techniques", Analytical Biochemistry, 162:89–101 (1987).

Halfman, et al., "Homogeneous, Micelle Quenching Fluoroimmunoassay for Detecting Amphetamines in Urine", Clinical Chemistry, 32/9, 1677–1681 (1986).

"Single-Reagent Polarization Fluoroimmunoassay for Amphetamine in Urine", Chemical Abstracts, vol. 103, Aug. 26, 1985, p. 8, Abstract No. 64284y.

Eramin, S. A., et al., "Single-Reagent Polarization Fluoroimmunoassay of Methamphetamine in Urine," Clinical Chemistry, 33(10):1903–1906 (1987).

Colbert, D. L., "Single-Reagent Polarization Fluoroimmunoassay for Aphetamine in Urine," Clinical Chemistry, 33(7):1193–1195 (1985).

Cheng, L. T., "Amphetamines New Radioimmunoassay," FEBS Letters, 36(3), Nov. 1973.

Riceberg, Louis J., et al., "Estimation of $\beta$-3,4-Dimethoxyphenethylamine and Related Compounds in Urine Extracts By Radioimmunoassay," Biochemistry Pharmacology, vol. 24, 259–265 (1975).

Faraj, Bahjat A., et al., "Specificity of an Antibody Directed Against d-Methamphetamine Studies with Rigid and Nonrigid Analogs," Journal of Medical Chem. 19:1 pp. 20–25 (1976).

Molina, C., et al., "An FPIA Specific for Amphetamine and Methamphetamine," Clinical Chemistry, 31:6, 941–942 (1985).

"The Radioimmunoassay for Methamphetamine", Chem. Pharm. Bull. 25(4) 840–842 (1977).

Kanda, Yukio, et al., "Studies on Immunoassay for Methamphetamine", 31:3 (1978).

Riceberg, Louis J., et al., "Radioimmunoassays of 3,4,5-Trimethoxyphenethylamine (Mescaline) and 2,5-Dimethoxy-4-Methylphenyl-isopropylamine(-DOM)," Analytical Biochemistry, 60:551–559 (1974).

Cheng, L. T. et al., "Amphetamines: New Radioimmunoassay," FEBS Letters, 36:3, 339–342 (Nov. 1973).

Inayama, Seiichi, et al., "The Radioimmunoassay for Methamphetamine," Chem. Pharm. Bull., 25(4) 840–842 (1977).

Aoki, Kimiko, et al., "A Screening Method for Urinary Methamphetamine—Latex Agglutination Inhibition Reaction Test," Forensic Science International, 27 p. 49–56, (1985).

Tokura, Seichi, et al., "Induction of Methamphetamine-Specific Antibody Using Biodegradable Carboxymethly-chitin," Analytical Biochemistry 161:117–112 (1987).

Tamaki, Yoshihiro, et al., "Solid-Phase MicroELISA for Methamphetamine," JPN J Legal Med., 37:4, 417–420 (1983).

Ishiyama, Ikuo, et al., "Histochemical Demonstration of Methaphetamine by Immunocytochemistry," Journal of Forensic Sciences, 32:3 658 (1987).

Inayama, Seiichi, et al., "Preparation of a Specific Antibody to Methamphetamine," Chem. Pharm. Bull., 25:4, 840 (1977).

Budd, Robert D., "Amphetamine EMIT-Structure Versus Reactivity," Clinical Toxicology, 18:1, 91–110 (1981).

Budd, Robert D., "Amphetamine Radioimmunoassay-Structure Versus Reactivity," 18:3, 299–316 (1981).

METHOD AND REAGENTS FOR DETECTING AMPHETAMINE AND/OR D-METHAMPHETAMINE IN BIOLOGICAL SAMPLES

This application is a continuation of application Ser. No. 07/265,361, filed Oct. 28, 1988, now abandoned.

BACKGROUND OF THE INVENTION

1. Technical Field

The present invention generally relates to a fluorescence polarization immunoassay, and reagents useful therein, for amphetamine and d-methamphetamine. It provides a preincubation step which is effective to eliminate cross reactivity to $\beta$-hydroxyamines. In addition, it relates to the elimination of potential flu rescence interference by riboflavin and potential interference by endogeneous tyramine. Further, the particular methods of chemically synthesizing the novel chemical reagents employed in the novel fluorescence polarization immunoassay of the instant invention eliminate the necessity of utilizing "controlled substances" as starting materials and, thus, eliminate the significant time, effort, and expense which is necessary in order to comply with requirements of the United States Drug Enforcement Agency (USDEA).

2. Background Art

Amphetamine and methamphetamine, the structural chemical formulas of which are presented below, are sympathomimetic phenethylamine derivatives having central nervous system stimulant activity.

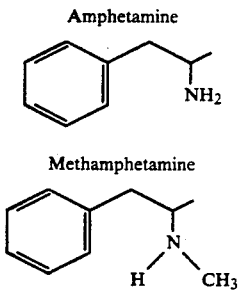

Amphetamine

Methamphetamine

These drugs have been used for the treatment of obesity, narcolepsy, and hypotension. However, excessive or prolonged use of these drugs may lead to tolerance and physical dependence. Because of their stimulant effects, the drugs are commonly sold illicitly and abused. Physiological symptoms often associated with very high amounts of ingested amphetamine and methamphetamine include elevated blood pressure, dilated pupils, hyperthermia, convulsions, and acute amphetamine psychosis.

The biological fluid tested most frequently for abuse of amphetamine and methamphetamineis is urine. Other biological fluids have not been extensively investigated for use in assays for the detection of amphetamine and methamphetamine.

In the past, amphetamines have been detected by a number of techniques, including thin layer chromatography (TLC), gas chromatography (GC), and high performance liquid chromatography (HPLC). These methods generally involve chemical extractions of the drugs, complicated procedures requiring highly trained personnel and lengthy assay times. Thin layer chromatography is labor intensive and lacks sensitivity. Gas chromatography and high performance liquid chromatography, each of which is also labor intensive, require highly trained personnel to carry out extractions of the analyte from the biological matrix. In addition, gas chromatography normally requires a derivatization step.

In general, competitive binding immunoassays have provided a preferable alternative to physical methods such as gas chromatography and high performance liquid chromatography.

Fluorescence polarization immunoassay procedures provide a reliable quantitative means for measuring the amount of tracer antibody complex produced in a homogeneous competitive binding assay.

Typically, competitive binding immunoassays are used for measuring ligands in a test sample. Generally, a "ligand" is a substance of biological interest to be determined quantitatively by a competitive binding immunoassay technique. The ligands compete with a labeled reagent, or "ligand analog," or "tracer," for a limited number of receptor binding sites on antibodies specific to the ligand and ligand analog. The concentration of ligand in the sample determines the amount of ligand analog which binds to the antibody. The amount of ligand analog that will bind to the antibody is inversely proportional to the concentration of ligand in the sample, because the ligand and the ligand analog each bind to the antibody in proportion to their respective concentrations.

Fluorescence polarization provides a quantitative or qualitative means for measuring the amount of tracer antibody conjugate produced in a competitive binding immunoassay. Fluorescence polarization techniques are based on the principle that a fluorescent-labeled compound, when excited by plane polarized light, will emit fluorescence having a degree of polarization inversely related to its rate of rotation. Accordingly, when a tracer-antibody conjugate having a fluorescent label is excited with plane polarized light, the emitted light remains highly polarized because the fluorophore is constrained from rotating between the time that light is absorbed and emitted. In contrast, when an unbound tracer is excited by plane-polarized light, its rotation is much faster than the corresponding tracer-antibody conjugate and an excited population of molecules is randomized much more quickly. As a result, the light emitted from the unbound tracer molecules is depolarized.

Such fluorescence polarization techniques have been applied in U.S. Pat. No. 4,420,568 to Wang, et al., which is directed to the use of a triazinylamino-fluorescein moiety as the fluorophore.

An accurate and reliable immunoassay for abuse of amphetamine and d methamphetamine requires that antibody "cross-reactivity" (recognition of compounds other than the desired ligand or ligands) be minimized.

In particular, although both the d- and l-enantiomers of methamphetamine are USDEA Schedule II controlled substances and, thus, are both considered to have abuse potential, the l-enantiomer has weaker stimulant activity and is contained in small amounts in some over-the counter medications. It is therefor considered undesirable for an assay which is employed to detect drug abuse to respond to l-methamphetamine alone in a sample. Therefor, the cross-reactivity for l-methamphetamine in such an assay should be as close as possible to zero. The combination of novel antisera and tracers employed in the immunoassay of the present invention reduces the cross-reactivity for 1-methamphetamine to below 5.1%.

It is also known that derivatives of β-phenethylamine, particularly β-hydroxyphenethylamine compounds, may be strong interferants in an immunoassay for amphetamine and methamphetamine. One such β-hydroxyphenethylamine, the drug phenylpropanolamine, is found frequently in decongestants sold over the counter. U.S. Pat. No. 3,856,469 discloses removal of β-hydroxyphenethylamine interference from a sample intended for amphetamine or methamphetamine analysis by treating the sample at a pH greater than 8.0 with an amount of aqueous periodate in the presence of ammonium hydroxide. In addition to requiring sample treatment at a basic pH, the aqueous pretreatment in U.S. Pat. No. 3,856,469 is suggested as useful only preceeding sample evaluation by thin layer chromatography and immunoassays by radioimmunoassay, electron spin resonance technique or enzyme technique.

In addition, tyramine, which may be present naturally in a biological sample being analyzed for amphetamine and/or methamphetamine, may also be a strong interferant in an immunoassay for amphetamine and d-methamphetamine. The undesirable result associated with tyramine interference is that false positive results may be obtained. However, the combination of novel antisera and tracers employed in the immunoassay of the present invention significantly improves the selectivity of this immunoassay for amphetamine and d methamphetamine over tyramine in comparison with those methods described in the art in that it maintains the cross-reactivity of the immunoassay for tyramine at about 0.4%.

Further, the particular methods of chemically synthesizing the novel chemical reagents employed in the novel fluorescence polarization immunoassay of the instant invention eliminate the necessity of utilizing "controlled substances" as starting materials and, thus, eliminate the significant time, effort, and expense which is necessary in order to comply with requirements of the federal Drug Enforcement Agency.

Finally, the immunoassay of the present invention provides a more rapid and accurate amphetamine/d methamphetamine assay method than prior art methods because it requires no specimen treatment before analysis and because the assay system has minimal cross-reactivity to 1-methamphetamine or other amphetamine like compounds.

For art relating to the detection of amphetamine and methamphetamine in biological samples, see U.S. Pat. No. 3,996,344 (phenethylamine antigenic conjugates, their preparation, antibodies and use); U.S. Pat. No. 4,016,146 (phenethylamine antigenic conjugates, their preparation, antibodies and use); U.S. Pat. No. 4,041,076 (immunoassay for pharmacologically active phenethylamines); U.S. Pat. No. 4,329,281 (hapten compositions employed in preparing immunogens which are employed in the elicitation of antibodies selective to amphetamine and methamphetamine); U.S. Pat. No. 3,966,764 (ligand determination of spin labeled compounds by receptor displacement-amphetamine analogs); U.S. Pat. No. 4,067,774 (compounds for enzyme amplification assay), U.S. Pat. No. 3,878,187 (polypeptide derivatives of amphetamine and analogs for immunoassays); FEBS LETTERS 36, 3 1973) (radioimmunoassay procedure for measuring amphetamines in urine); Chem. Pharm. Bull. 25(4), 840 (1977) (radioimmunoassay for methamphetamine); Forensic Science International 27, 49 ( 985) (a latex agglutination inhibition reaction test for screening urinary amphetamine); Analytical Biochemistry 161, 117 (1987) (the induction of methamphetamine-specific antibody using biodegradable carboxymethyl-chitin); Journal of Medicinal Chemistry, Vol. 19, No. 1 (1976) (determination of the specificity of an antibody directed against d-(S)-methamphetamine); Clin. Chem. 32/9, 1677 (1986)(a homogeneous fluoroimmunoassay for detecting amphetamines in urine ; Jpn J Legal Med 37(4), 417 (1983) (solid phase micro-ELISA for methamphetamine); Journal of Forensic Sciences, Vol. 32, No. 3, 658 (1987) (histochemical demonstration of methamphetamine by immunocytochemistry); Chem. Pharm. Bull. 25(4), 838 (1977) (preparation of a specific antibody to methamphetamine); Clinical Toxicology, 18(1), 91 (1981) (analysis of amphetamine-related amines by EMIT at different concentrations); Analytical Biochemistry 60, 551 (1974) (radioimmunoassay of 3,4,5 -Trimethoxy phenethylamine (mescaline) and 2,5-Dimethoxy 4-Methylphenyl-isopropylamine); and Clinical Toxicology, 18(3), 299 (1981) (analysis of amphetamine-related amines by RIA).

Accordingly, a need exists for providing a method and reagents for performing a reliable and accurate fluorescence polarization assay for both amphetamine and d-methamphetamine in biological fluids such as urine. The present invention is an advance in the art in that novel reagents specifically useful in fluorescence polarization immunoassays for amphetamine and d-methamphetamine, and a novel combination of such reagents in such immunoassays, are provided.

SUMMARY OF THE INVENTION

The present invention relates to a method for detecting the presence, and determining the approximate quantity, of both amphetamine and d-methamphetamine in biological samples utilizing fluorescence polarization techniques. In particular, the method of the present invention involves preincubation of a urine sample to be tested for amphetamine and/or d-methamphetamine without adjustment of the sample's pH to alkaline conditions. Particularly, a sample is treated solely with an aqueous periodate solution, having a pH from about 4.0 to 7.5, to eliminate undesirable compounds which cross react with antibodies specific for amphetamine and/or d-methamphetamine and the ligand analogs thereof.

The treated sample is intermixed with a composition comprising a first fluorescein or fluorescein derivative tracer compound coupled to a ligand analog of amphetamine, a second fluorescein or fluorescein derivative tracer compound coupled to a ligand analog of d-methamphetamine, a first antibody capable of specifically recognizing and binding amphetamine and the first tracer compound and a second antibody capable of specifically recognizing and binding d-methamphetamine and the second tracer compound. The amount of the first and second tracer compounds bound to the first and second antibodies, respectively, is determined by fluorescence polarization techniques as a measure of the amount of amphetamine and d-methamphetamine in the biological sample.

Further, the present invention relates to the elimination of potential fluorescence interference by riboflavin (vitamin $B_2$). Riboflavin, which is an essential nutrient for man, is the heat stable factor of the vitamin B complex, 6,7-dimethyl-9-[1'-D-ribityl]isoalloxazin, $C_{17}H_{20}N_4O_6$, and occurs in milk, muscle, liver, kidney, eggs, grass, malt, leafy young vegetables, and various algae. Riboflavin binding protein (RBP) is added either directly to each sample or to one or more of the reagents utilized in the assay, wherein it binds all riboflavin present into riboflavin binding protein-riboflavin complexes, thus eliminating fluorescence interference. Other fluorescence-quenching substances may also be utilized for this purpose.

The present invention also relates to the elimination of potential interference by endogeneous tyramine. Tyrosine is an amino acid which is found in most proteins and which is synthesized metabolically from phenylalanine. Tyramine is a decarboxylation product of tyrosine and appears in urine as excreted. It is also a component of some foods, such as various cheeses, and is a product of bacterial degradation. Since even a small amount of cross-reactivity (Ex. 2%) of the antiserum employed in an immunoassay for amphetamine and d-methamphetamine with tyramine present in a sample of biological fluid may result in a false positive result for amphetamine and/or d-methamphetamine when a urine sample contains a substantial amount of tyramine, an accurate and reliable immunoassay for amphetamine and d-methamphetamine requires that antibody cross-reactivity with tyramine be minimized. It was unexpectedly found that the combination of novel antiserum and tracers employed in the immunoassay of the present invention significantly improves the selectivity of this immunoassay for amphetamine and d-methamphetamine over tyramine in comparison with those methods described in the art in that it maintains the cross-reactivity of the immunoassay for tyramine at about 0.4%.

The present invention further relates to a stabilized reagent kit useful for determining amphetamine and d-methamphetamine in a single assay including novel tracers and salts thereof, which are useful as reagents in the novel method of the present invention. Other components of the reagent kit in accordance with the invention include a solution containing riboflavin binding protein, an aqueous pretreatment solution having an amount of periodate effective in eliminating undesirable cross-reactivity to β-hydroxyphenethylamines and an antibody reagent with a composition comprising a first antibody capable of specifically recognizing and binding amphetamine and a second antibody specifically recognizing and binding d-methamphetamine. In the case of automated fluorescence polarization assays utilizing automated dispensing means such as a pipette, the present invention provides for a post-mixing washing of the dispensing means with an aqueous propylene glycol and saline solution to minimize drug carryover from one sample to other samples resulting from adhesion to the dispensing means. The preferred aqueous pretreatment solution is from about 0.1 to 0.25 molar sodium periodate.

Further objects and attendant advantages of the invention will be best understood from a reading of the following detailed description taken together with the drawings and the Examples.

DETAILED DESCRIPTION OF THE INVENTION

Definitions

The term "ligand", as used herein, refers to a molecule, to which a binding protein, such as a receptor or an antibody, can be obtained or formed. The ligands of interest in the present invention are phenethylamines, more particularly, amphetamine and d-methamphetamine. Such ligands are protein-free compounds of low molecular weight which do not normally induce antibody formation when injected into an animal but which are reactive with antibodies. Ligands which are chemically modified for conjugation to a carrier protein are termed haptens. Antibodies to haptens are generally raised by first conjugating the haptens to a carrier and injecting the conjugate product into an animal. The resulting antibodies may be isolated by conventional, well-known antibody isolation techniques.

The term "ligand-analog", as used herein, refers to a mono- or polyvalent radical, a substantial portion of which has the same spatial and polar organization as the ligand to define one or more determinant or epitopic sites capable of competing with the ligand for the binding sites of a receptor. A characteristic of such a ligand-analog is that it possesses sufficient structural similarity to the ligand of interest as to be recognized by the antibody against the ligand. Generally, the ligand analog will have the same or substantially the same structure and charge distribution (spatial and polar organization) as the ligand(s) of interest (for purposes of the present invention, amphetamine and d-methamphetamine) for a significant portion of the molecular surface. Frequently, the linking site for a hapten will be the same in preparing the antigen for production of antibodies as that used in the tracer for linking to the ligand, the same portion of the ligand analog which provides the template for the antibody will be exposed by the ligand analog in the tracer.

The present invention involves the use of fluorescein and derivatives of fluorescein. A necessary property of fluorescein and its derivatives for the usefulness of the tracer compounds herein is the fluorescence of fluorescein. Fluorescein exists in either of two tautomeric forms shown below, depending on the acid concentration (pH) of the environment.

Alternate Structural Formulae and Names of the Fluorescein Moiety included in the Novel Tracers of the Present Invention

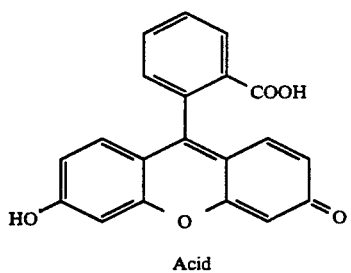

Acid

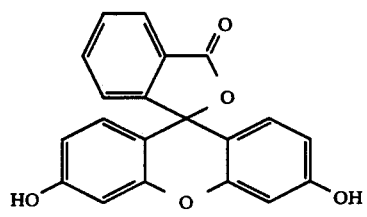

Lactone

In the open (acid) form, there are a number of conjugated double bonds which make that form of fluorescein (and compounds containing a fluorescein moiety) capable of absorbing blue light and emitting green fluorescence after an excited state lifetime of about 4 nanoseconds. When the open and closed forms coexist, the relative concentration of molecules in the open and closed forms is easily altered by adjustment of the pH level. Generally, the tracer compounds of the present invention exist in solution as salts such as sodium, potassium, ammonium and the like, allowing the compounds to exist in the open, fluorescent form, when employed in the novel analytical methods of the present invention. The specific salt present will depend on the buffer employed to adjust the pH level. For example, in the presence of a sodium phosphate buffer, the compounds of the present invention will generally exist in the open form, as a sodium salt.

As used herein, the term "fluorescein," either as an individual compound or as a component of a larger compound, is meant to include both the open and closed forms, if they exist for a particular molecule, except in the context of fluorescence. An open form is necessary for the fluorescence to occur.

The numbering of carbon atoms of the fluorescein molecule varies, depending upon whether the open or closed form of the molecule is considered. Accordingly, the literature concerning fluorescein and its compounds is not uniform as to carbon atom numbering. In the closed form, the carbon para to the carboxylic acid group on the isolated phenyl ring is numbered 5. For purposes of this disclosure, the numbering of the closed form is adopted because the raw materials used in the syntheses are most popularly numbered with that system. The carbon atom of fluorescein and its derivatives para to the carboxyl group is therefore numbered "6" for the purposes of the present disclosure.

A tracer in solution which is not complexed to an antibody is free to rotate in less than the time required for absorption and re-emission of fluorescent light. As a result, the re-emitted light is relatively randomly oriented so that the fluorescence polarization of a tracer not complexed to an antibody is low, approaching zero. Upon complexing with a specific antibody, the tracer-antibody complex thus formed assumes the rotation rate of the antibody molecule which is slower than that of the relatively small tracer molecule, thereby increasing the polarization observed. Therefore, when a ligand competes with the tracer for antibody sites, the observed polarization of fluorescence of the resulting mixture of the free tracer and tracer-antibody complex assumes a value intermediate between that of the tracer and that of the tracer-antibody complex. If a sample contains a high concentration of the ligand, the observed polarization value is closer to that of the free tracer, i.e., low. If it contains a low concentration of the ligand, the polarization value is closer to that of the bound tracer, i.e., high. By sequentially exciting the reaction mixture of an immunoassay with vertically and then horizontally polarized light and analyzing only the vertical component of the emitted light, the polarization of fluorescence in the reaction mixture may be accurately determined. The precise relationship between polarization and concentration of the ligand to be determined is established by measuring the polarization values of calibrators with known concentrations. The concentration of the ligand can be extrapolated from a standard curve prepared in this manner.

The particular tracers formed in accordance with this invention have been found to produce surprisingly good assays, as will be demonstrated infra.

The Reagents

The Controlled Substances Act is a set of federal laws which regulate the prescribing and dispensing of psychoactive drugs, including narcotics, according to five schedules based on their abusive potential, medical acceptance and ability to produce dependence. This Act also establishes a regulatory system for the manufacture, storage, and transport of the drugs in each schedule. Drugs covered by this Act include opium and its derivatives, opiates, hallucinogens, depressants and stimulants. When controlled substances, or substances which have the capacity to affect behavior, and which are regulated by law with respect to possession and use, such as amphetamine and methamphetamine, are employed as starting materials in the synthesis of chemical compounds, or are produced as intermediates or final products in this chemical synthesis, a significant amount of time and effort must be spent preparing and filing the appropriate paperwork with the federal Drug Enforcement Agency. In addition, the controlled substances must be used in a "controlled," or highly regulated, manner, requiring extraordinary security in the operation of laboratory and manufacturing facilities. Thus, in order to avoid the time, effort, and expense which is necessary in order to conform to various requirements of the Drug Enforcement Agency, such as maintaining detailed inventories and keeping all controlled substances locked up, it is extremely desirable to avoid the use, or production of, controlled substances when performing chemical reactions and synthesizing chemical compounds. The particular methods of chemically synthesizing the novel chemical reagents employed in the novel fluorescence polarization immunoassay of the instant invention are advantageous in that they eliminate the necessity of utilizing controlled substances as starting materials and, thus, eliminate the significant time, effort, and expense which is necessary in order to comply with requirements of the federal Drug Enforcement Agency.

The objective in designing a Fluorescence Polarization Immunoassay is to have competition between the desired phenethylamines and the tracers for the recognition sites of the antibody. Great variations in the structure of the haptens and tracers are allowed in achieving this goal. For purposes of this invention, "haptens" are precursors of the immunogens or tracers, comprising generally a substituted phenethylamine derivative and a linking group to the protein carrier or fluorescein compound, or derivative thereof.

1. Pretreatment Reagent

An important aspect of the present invention is the elimination of cross-reactivity to $\beta$-hydroxyphenethylamines in a fluorescence polarization assay by pretreating the test sample with an effective amount of an aqueous periodate solution. Specifically, the aqueous periodate solution causes cleavage of the side chain between the alpha and beta-carbon when there is a hydroxyl group (—OH) attached to the alpha-carbon. Thus, the compound no longer competes for the binding sites.

The pretreatment reagent in accordance with the reagent kit of the present invention includes an aqueous periodate solution having a pH from about 4 to 7.5. Preferably, the pretreatment solution includes 0.1 to 0.25 M of sodium periodate having a pH range from about 4.0 to 5.0. Most preferably the sodium periodate solution includes about 0.20 M sodium periodate having a pH of about 4.5. Surprisingly, it has been found that pretreatment of a test sample can be conducted without the need for pH adjustment of the test sample to alkaline conditions with compounds such as hydroxides.

2. The Tracers a. The Structure of the Tracers

Useable tracers can be produced from a wide variety of phenethylamine derivatives. The first novel amphetamine tracer compound of the present invention is preferably of Formula 1:

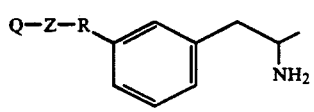

Formula 1 and the second novel amphetamine tracer compound of the instant invention is preferably of Formula 2:

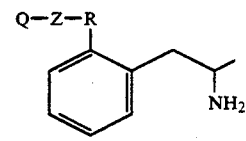

Formula 2 wherein, for both Formulas 1 and 2:
(1) Q is
  (a) fluorescein; or
  (b) a derivative of fluorescein;
(2) Z is >NH, >C=O or >SO$_2$; and
(3) R is a linking group including up to 5 heteroatoms and having a total of from 0 to 15 carbon atoms and heteroatoms.

The novel d-methamphetamine tracer compound of the present invention is preferably of Formula 3:

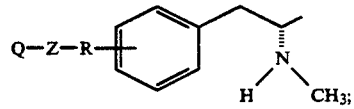

wherein:
(1) Q is
  (a) fluorescein; or
  (b) a derivative of fluorescein;
(2) Z is >NH, >C=O or >SO$_2$; and
(3) R is a linking group including up to 5 heteroatoms and having a total of from 0 to 15 carbon atoms and heteroatoms.

Structures 1 through 10 represent structures of the preferred novel tracers of amphetamine and d-methamphetamine in accordance with the present invention:

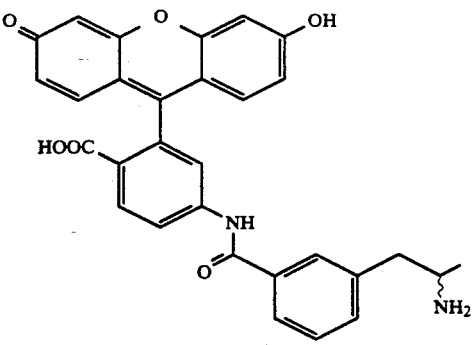

Structure 1

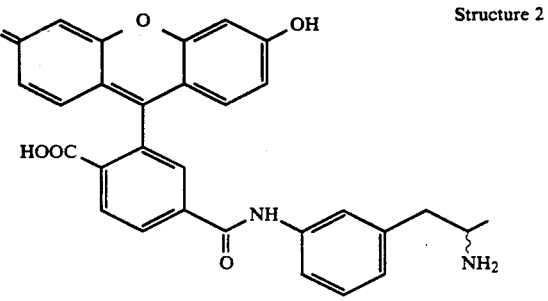

Structure 2

Structure 3

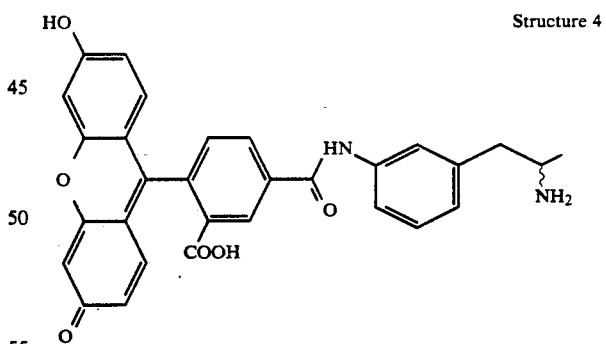

Structure 4

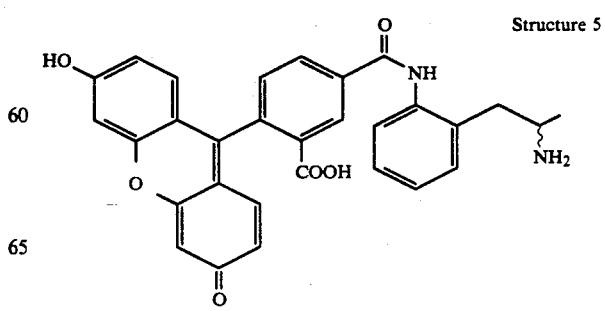

Structure 5

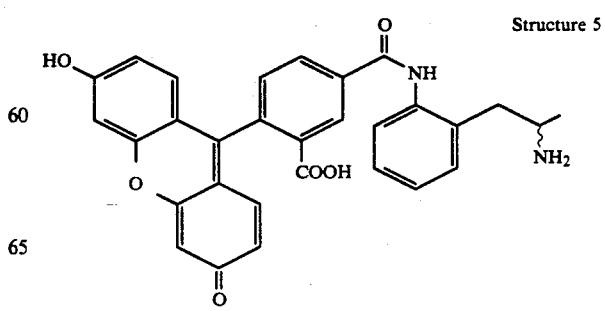

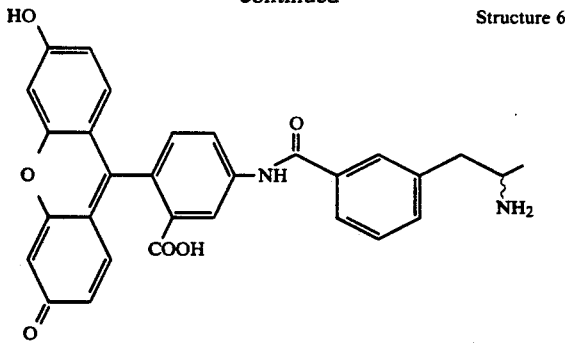
Structure 6

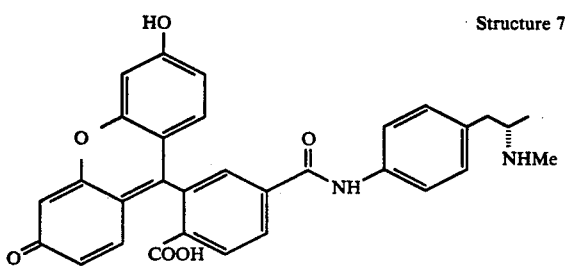
Structure 7

Structure 8

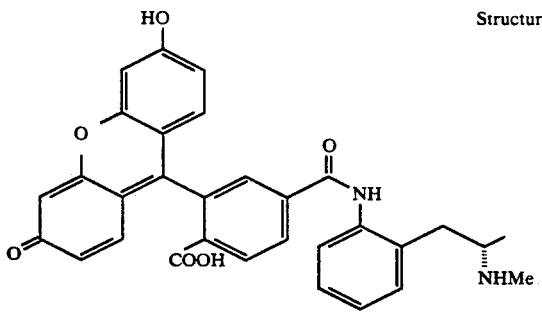
Structure 9

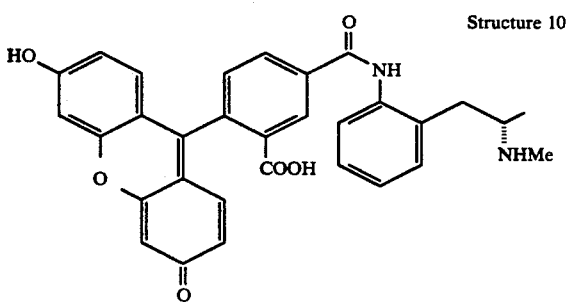
Structure 10

The tracer is a phenylethylamine derivative which is linked to a fluorescein derivative by, for example, an amido, amidino, triazinylamino, carbamido, thiocarbamido, carbamoyl, thiocarbamoyl, or sulfonylcarbamoyl group, as shown below. The tracers are prepared by linking the appropriate fluorescein derivative to a phenylethylamine derivative containing an amino, carboxylic acid, isocyanate, chlorosulfonyl, or the like group, as will be discussed in the context of the synthetic method and the Examples below. For illustrative purposes, some of the various linking groups which may be employed to couple the fluorescein moiety to the phenylethylamine derivative are presented below. The symbol "Fl" represents a fluorescein moiety.

Linking Groups

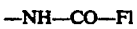

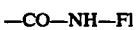

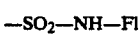

By way of example, the following are some of the fluorescein derivatives which may be employed to synthesize the novel tracers of the present invention:

| | |
|---|---|
| Fl—NH$_2$ | fluorescein amine |
| Fl—CO$_2$H | carboxyfluorescein |
| Fl—NHCOCH$_2$I | alpha-iodoacetamidofluorescein |
| Fl—CH$_2$NH$_2$ | aminomethylfluorescein |

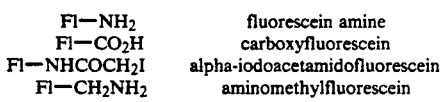

2,4-dichloro-1,3,5,-triazin-2-yl amino-fluorescein (DTAF)

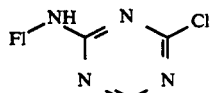

4-chloro-6-methoxy-1,3,5-triazin-2-ylamino fluorescein (Methoxy DTAF)

The novel amphetamine tracer precursor compounds of the present invention also preferably have the structural formulas shown in Formulas 4 and 5 below:

Formula 4

Formula 5 wherein, for both Formulas 4 and 5:

(1) Q is hydrogen, hydroxyl or a leaving group; [For purposes of this patent application, a "leaving group" is defined as a halogen, an acyloxy group (including a carbonate ester), a succinimidyloxyl or phthalimidyloxy group, an alkoxy or phenoxy or substituted phenoxy group, an imidazolyl group, a benzotriazolyloxy group or any of the other similar activating groups well known to those of skill in the art.]

(2) Z is >NH, >C=O or >SO₂; and
(3) R is a linking group including up to 5 heteroatoms and having a total of from 0 to 15 carbon atoms and heteroatoms.

The novel methamphetamine tracer precursor compounds of the present invention also preferably have the following structural formula:

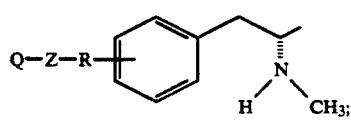

wherein:
(1) Q is hydrogen, hydroxyl or a leaving group;
(2) Z is >NH, >C=O or >SO₂; and
(3) R is a linking group including up to 5 heteroatoms and having a total of from 0 to 15 carbon atoms and heteroatoms.

Exemplary structures of some of the haptens which may be employed to form the novel tracer and immunogen compounds in accordance with the present invention are presented in Structures 11 through 16:

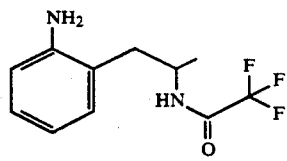

Structure 11

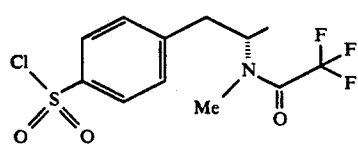

Structure 12

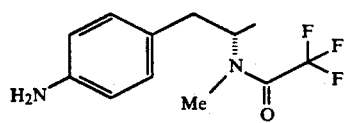

Structure 13

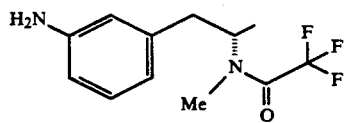

Structure 14

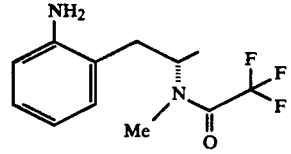

Structure 15

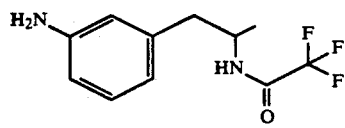

Structure 16 b. The Synthesis of the Tracers

The tracers of the present invention are made by coupling a fluorescein moiety, or a derivative of fluorescein, to the general structure shown in Structures 3 and 4.

The fluorescein moiety can be linked to the amino, carboxyl, chlorosulfonyl, imidate or alkoxy functional group by an amide, an amidine, an urea, a thiourea, a carbamate, a thiocarbamate, triazinylamino, sulfonamide, or sulfonylcarbamate linkage, as shown above In the presently preferred embodiment for amphetamine, the fluorescein derivative is 6-aminofluorescein and this is coupled to a precursor of the tracer shown below.

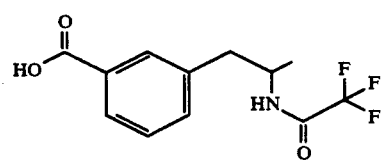

The 3-carboxyamphetamine trifluoroacetamide is converted to the corresponding acid chloride by treatment with oxalyl chloride, and this is coupled to 6-aminofluorescein in acetonitrile solution. Other activating reagents, such as chloroformates or acid chlorides or anhydrides (which form mixed anhydrides with the carboxylic acid precursor), or 1-hydrox-ybenzotriazole, p-nitrophenol, pentafluorophenol, imidazole, and the like, together with a dehydrating reagent, can be used. Other solvents, such as dimethylformamide and dimethoxyethane, can be used. The reactants are preferably coupled under conditions for forming amide linkages. It is most preferred that a procedure involving conversion to an acid chloride be used. The compound is then preferably deprotected by hydrolysis with potassium carbonate in an aqueous methanol solution. Other reagents appropriate for the hydrolysis of trifluoroacetamides, such as a tertiary amine base, sodium carbonate or an alkali metal hydroxide or the like, may be employed for the deprotection step.

The preferred embodiment for the amphetamine and d-methamphetamine tracers are presented in Structures 17 and 18, respectively:

Structure 17

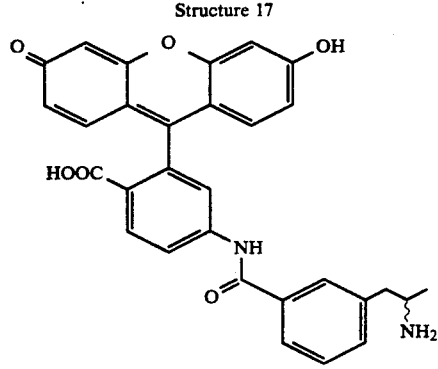

Structure 18

-continued

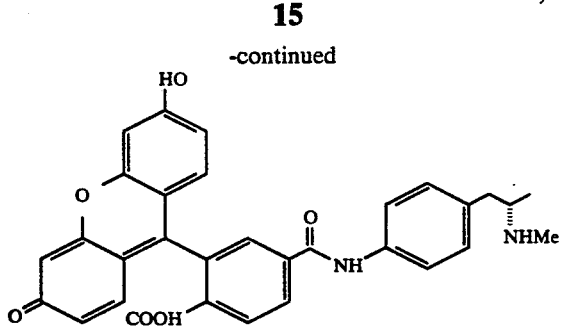

For the d-methamphetamine tracer, the fluorescein derivative is 6-carboxyfluorescein. This is coupled to the precursor shown in FIG. 19;

Structure 19

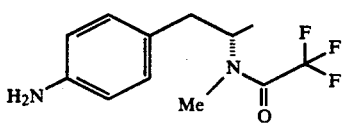

The 6-carboxyfluorescein is preferably coupled with the 4-amino-d-methamphetamine trifluoroacetamide by treatment with bis(2-oxo-3-oxazolidinyl)phosphinic chloride int he presence of a tertiary amine base in acetonitrile solution. Other activating reagents, such as chloroformates or acid chlorides or anhydrides (which form mixed anhydrides with the carboxylic acid precursor), or 1-hydroxybenzotriazole, p-nitrophenol, pentafluorophenol, imidazole, and the like, together with a dehydrating reagent, can be used. The reactants are preferably coupled under conditions for forming amide linkages. It is most preferred that a procedure involving bis(2-oxo-3-oxazolidinyl)phosphinic chloride be employed. The compound is then preferably deprotected by hydrolysis with potassium carbonate in an aqueous methanol solution. Other reagents appropriate for the hydrolysis of trifluoroacetamides, such as a tertiary amine base, sodium carbonate or an alkali metal hydroxide or the like, may be employed for the deprotection step.

Usable tracers can be prepared from a variety of phenylethylamine derivatives.

All phenylethylamine derivatives that have a terminal amino group, such as amino, hydrazinyl, hydrazido or the like, are coupled to carboxyfluorescein by the active ester method or the mixed anhydride method, and coupled to DTAF or alkoxy DTAF by simply mixing the two materials in solution. The amino group can be converted to the isocyanate and thioisocyanate groups by reaction with phosgene and thiophosgene, respectively. These are then condensed with fluoresceinamine or 4'-aminomethylfluorescein to produce the tracer.

All phenylethylamine derivatives that have a terminal chlorosulfonyl group are coupled to 4'-aminomethylfluorescein or fluoresceinamine by simply mixing the two materials in solution and using a base to remove the acid that is generated.

All phenylethylamine derivatives that have a terminal carboxylic acid group, such as carboxylic acid, (aminohydroxy)alkylcarboxylic acid or the like, are coupled to 4'-aminomethylfluorescein or aminofluorescein by forming the acid chloride, making a mixed anhydride, or by the active ester method.

c. Combination of Tracers

According to the present invention, the preferred tracer reagent is a composition comprising salts of a first tracer and a second tracer. Generally, the first tracer is a salt of a ligand analog to amphetamine and the second tracer is a salt of a ligand analog to d-methamphetamine. The combination of individual tracers for amphetamine and for methamphetamine provides the advantage of detection of both drugs (amphetamine/d-methamphetamine) while maintaining high specificity, low cross-reactivity, high sensitivity and accuracy. Numerous combinations of amphetamine tracers with d-methamphetamine tracers formed in accordance with the above described procedures may be used. Preferably, the first and second tracers are salts of sodium, potassium, ammonium and the like. Most preferably, the first and second tracers exist in the reagent solution as sodium salts and the first tracer is the ligand analog of amphetamine shown in Structure 1 and the second tracer is the ligand analog of d-methamphetamine shown in Structure 7. The tracer formula presently preferred is about 90 nanomolar of the mixed tracers in 0.1 molar sodium phosphate buffer at pH 7.5, 1% sodium azide, and 0.01% bovine gamma globulin.

3. The Antibodies

The antibodies of the present invention are prepared by developing a response in animals to the immunogens described below. The immunogen is administered to animals such as rabbits or sheep by a series of injections, in a manner well-known to those skilled in the art.

a. The Structure of the Immunogens

Usable antibodies can be produced from a variety of phenethylamine derivatives. Immunogens prepared from phenethylamine compounds functionalized at the para position can produce antibodies in animals. Such antibodies are useful in an assay for phenethylamines according to the invention when combined with the appropriate tracer.

The antibodies to amphetamine and d-methamphetamine employed in the assay are raised in response to amphetamine and d-methamphetamine derivatives attached to a protein carrier (immunogens), preferably bovine serum albumin or bovine or porcine thyroglobulins. The novel amphetamine immunogen compounds of the present invention are preferably of Formulas 7 and 8:

Formula 7

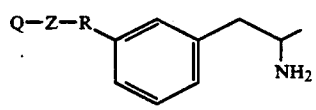

Formula 8

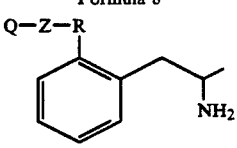

wherein, for both Formulas 7 and 8:
 (1) Q is
  (a) a poly(amino acid);
  (b) a poly(amino acid) derivative; or
  (c) another immunogenic carrier;
 (2) Z is >NH, >C=O or >SO$_2$; and (3) R is a linking group including up to 5 heteroatoms and having a total of from 0 to 15 carbon atoms and heteroatoms.

The novel methamphetamine immunogen compound of the present invention is preferably of Formulas 9:

Formula 9

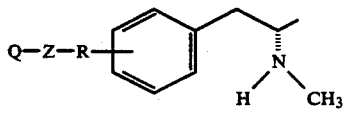

wherein:
(1) Q is
  (a) a poly(amino acid);
  (b) a poly(amino acid) derivative; or
  (c) another immunogenic carrier;
(2) Z is >NH, >C=O or >SO$_2$; and
(3) R is a linking group including up to 5 heteroatoms and having a total of from 0 to 15 carbon atoms and heteroatoms.

Structures 20 and 21 represent the structures of the preferred novel methamphetamine and amphetamine immunogen compounds, respectively, in accordance with the present invention:

Structure 21

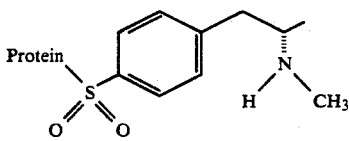

Structure 20

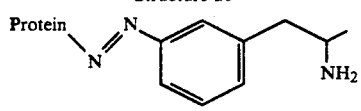

The immunogens of the present invention are prepared by coupling a phenethylamine hapten precursor compound of formulas 4 amphetamine, 5 amphetamine) or 6 (methamphetamine) with a protein or a protein derivative, as will be discussed in the context of the synthetic method and the Examples below.

In a preferred form of the invention, the immunogen is prepared by coupling the aforedescribed substituted phenethylamine compound with bovine thyroqlobulin. Various other protein carriers may also advantageously be used, e.g., keyhole limpet hemocyanin, egg ovalbumin, bovine gamma-globulin, serum albumin, and so forth. Alternatively, synthetic poly(amino acids) having a sufficient number of available amino groups can be employed, as can other synthetic or natural polymeric materials bearing functional groups reactive with amphetamine or d-methamphetamine haptens. The preferred immunogen precursor compounds according to the present invention are shown in Structures 22 and 23:

Structure 22

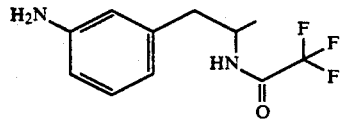

-continued
Structure 23

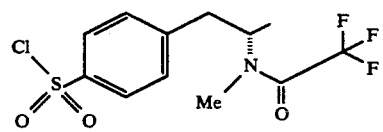

b. The Synthesis of the Immunogens

The immunogens of the present invention are made by coupling an amphetamine or d-methamphetamine derivative to a poly(amino acid).

In a preferred embodiment, the poly(amino acid) is bovine thyroglobulin, and the hapten can be selected from one of the exemplary structures shown above. These reactants are preferably coupled under conditions normally used to form amide, azo, sulfonamide, urea, and alkylamine linkages, and such conditions are well known to those skilled in the art. It is most preferred when carboxylic groups are employed as a partner in the coupling reaction that active ester procedures be used, as these are the most effective in forming the desired amide linkaqes in this context.

Before coupling the hapten to the poly(amino acid), the amine on the sidechain is protected. The protecting groups, for example, trifluoroacetyl or BOC (t-butylcarbamate), are added under conditions known to one skilled in the art.

The immunogens are prepared by coupling a hapten having its phenethylamino group protected and bearing an —NH$_2$, —CO$_2$H, —CONHNH$_2$, —CNOR, —CHO, —NCO or SO$_2$Cl group in the 2 or 3 position for a derivative of amphetamine or in the 2-, 3-, or 4-position for a derivative of d-methamphetamine, to a poly(amino acid). The sulfonyl chloride and isocyanate (—NCO) cases produce sulfonamide and urea or carbamate linkages, respectively. This is accomplished by direct coupling of the hapten to the poly(amino acid).

After coupling the sidechain amine-protected hapten to the protein, the protecting group is removed to provide the free amine or the amine in a salt form. When the protecting group employed is trifluoroacetyl, it can be removed by treatment with aqueous base, by exposure to aqueous sodium borohydride, or other conditions known to one skilled in the art. When the protecting group is BOC (t-butylcarbamate), it can be removed by aqueous acids, non aqueous acids, or other procedures known to one skilled in the art.

The syntheses of the above haptens are accomplished in very similar ways. The ideal starting material is a phenylethylamine, such as norephedrine or ephedrine or a compound which can be converted to a phenethylamine, such as a benzaldehyde or a phenylpropanol. If the sidechain amine functionality is originally present, or after it has been introduced, it must be rendered unreactive by a protecting group. After catalytic reduction of the nitro group to an amino group, it is then diazotized by reaction with cold nitrous acid. Carboxyl-containing haptens are activated using methods described above. In the case where Z-Q is SO$_2$Cl, protein coupling is effected by exposing an aqueous or aqueous-organic solution of protein to the chlorosulfonyl phenylethylamine derivative. After conjugation, the protecting groups are removed by methods known to one skilled in the art, and the immunogens are purified either by size exclusion chromatography or dialysis.

c. Combination of Antibodies

According to the present invention, the preferred antibody reagent is a composition comprising a first antibody raised in response to an immunogen described above, capable of recognizing and binding to amphetamine, and a second antibody, capable of recognizing and binding d-methamphetamine. Numerous combinations of antibodies raised in response to amphetamine or d-methamphetamine immunogens, in accordance with the above-described procedures, can be used provided that the antibodies are specific for amphetamine and/or d-methamphetamine. Most preferably, the antibody reagent includes an amount of the antibody raised in response to the immunogen shown in FIG. 20 and an amount of the antibody raised in response to the immunogen shown in Structure 21.

Rabbit, sheep or any other animal serum can serve as the source of antibodies for the antibody agent. The preferred antisera formula comprises sheep serum diluted with 0.1 molar sodium phosphate buffer at pH 7.5; 0.1% sodium azide; 0.01% bovine gamma globulin; 2% propylene glycol volume/volume); and 15 mg/ml riboflavin binding protein.

4. Wash Reagent

It has been surprisingly determined that providing a phenethylamine fluorescence assay reagent kit with an aqueous 5% propylene glycol and 0.45% NaCl wash reagent improves assay reliability and accuracy. Specifically, it has been found that providing a wash solution with about 5% propylene glycol and 0.45% NaCl reduces urine adhesion to dispensing means such as a probe, pipette, or syringe. It is to be understood that urine adhesion to the dispensing means can result in sample contamination yielding false positive results for samples tested subsequent to a phenethylamine-containing sample. In the case of highly automated assaying apparatus, such as the ABBOTT LABORATORIES' TD$_x$® Clinical Analyzer or the ABBOTT LABORATORIES' AD$_x$ TM Abused Drug System, both of which can test large numbers of samples sequentially, eliminating urine "carryover" between samples is highly desirable. Preferably, the reagent kit is provided with a wash solution including about 5% propylene glycol and 0.45% NaCl.

The Assay

The particular novel tracers and antibodies of the present invention have been found to produce excellent results in fluorescence polarization assays for the desired phenethylamine. As described above, it was surprisingly found that the combination of these novel tracers and antibodies in an immunoassay for amphetamine and d-methamphetamine eliminates the potential interference by endogeneous tyramine. The combination of antiserum and novel tracers employed in the immunoassay of the present invention significantly improves the selectivity of this immunoassay for amphetamine and d-methamphetamine in comparison with those methods described in the art in that it maintains the cross reactivity of the immunoassay for tyramine at about 0.4%, and the cross reactivity for l-methamphetamine below 5%.

Fluorescence interference by riboflavin (vitamin B2) may render the quantitation results of any assay for amphetamine and/or methamphetamine inaccurate. Thus, another significant advantage of the assay of the present invention is the elimination of potential fluorescence interference by riboflavin. This can be seen by an examination of the data contained in Table 1 below. Whereas the second and third columns represent data which was obtained before tracer was added to a drug-free urine sample (fluorescence intensity), the fourth and fifth columns represent data after the tracer was added to such sample (polarization).

TABLE 1

| Sample Number | Background (No Riboflavin Binding Protein) | Background (15 mg/mL Riboflavin Binding Protein) | (mP) Polarization (No Riboflavin Binding Protein) | (mP) Polarization (15 mg/mL Riboflavin Binding Protein) |
| --- | --- | --- | --- | --- |
| 02 | 4078 | 296 | 208.54 | 213.41 |
| 03 | 11859 | 632 | 222.14 | 210.29 |
| 04 | 8886 | 406 | 214.28 | 209.73 |
| 05 | 4180 | 227 | 204.17 | 208.29 |
| 07 | 19355 | 800 | 232.8 | 204.21 |
| 08 | 7784 | 418 | 207.84 | 206.34 |
| 09 | 8013 | 443 | 216.4 | 210.81 |
| 11 | 13927 | 469 | 231.76 | 213.1 |
| 12 | 6464 | 275 | 213.07 | 211.87 |
| 15 | 3966 | 654 | 211.85 | 213.45 |
| 16 | 1932 | 146 | 210.7 | 216.92 |
| 17 | 2782 | 368 | 207.72 | 213 |
| 20 | 8397 | 567 | 222.38 | 210.76 |
| 21 | 9662 | 423 | 218.18 | 212.24 |
| 23 | 7019 | 414 | 212.34 | 212.1 |
| Acal | 457 | 234 | 205.46 | 212.25 |

Further, the assay of the present invention provides a more rapid and accurate amphetamine and/or d-methamphetamine assay method than prior art methods because it requires no specimen treatment before analysis.

The general structures of the class of phenethylamines that can be quantitatively and/or qualitatively determined in accordance with the present invention are shown in Formulas 10 and 11:

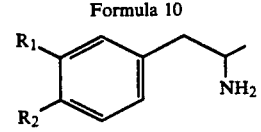

Formula 10

Formula 11

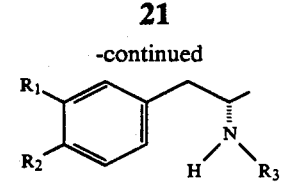

wherein, for both Formulas 10 and 11:

(1) $R_1$ and $R_2$ are hydrogen, chloro, methyl or methoxy, or are taken together to form a methylenedioxy bridge; and (2) $R_3$ is methyl or ethyl.

The assay of the present invention is a particularly desirable assay for amphetamine and/or d-methamphetamine because it detects amphetamine and d-methamphetamine, as well as certain USDEA Schedule 1 "designer drugs" (drugs which were specifically designed chemically to fall outside of the specific drug categories which had been previously regulated by the USDEA), such as 3,4-Methylenedioxyamphetamine, 3,4-Methylenedioxyethylamphetamine and 3,4-Methylene-dioxymethamphetamine. In addition, it fails to detect (1) amphetamine-like stimulant-type legitimate prescription drugs (non-USDEA-regulated drugs which may be considered to be false positives); and (2) nonstimulant drugs.

Cross reactivity was tested for amphetamine and methamphetamine and amphetamine metabolites. Compounds were assayed by adding a known quantity of the test compound to drug free normal human urine and assaying with the amphetamine/methamphetamine assay of the instant invention on the Abbott Laboratories' $TD_x$ ® Clinical Analyzer. The percent cross reactivity was determined by the following mathematical formula:

$$\% \text{ Cross-reactivity} = 100 \times \frac{\text{Concentration of Test Compound Found}}{\text{Concentration of Test Compound Added}}$$

Representative data are shown in Table 2 below.

TABLE 2

| Test Compound | Concentration Added (ug/mL) | Concentration Found (ug/mL) | % Cross Re-activity |
|---|---|---|---|
| l-Amphetamine | 8.0 | 2.33 | 29.1 |
| | 3.0 | 0.92 | 30.7 |
| | 1.0 | 0.36 | 36.0 |
| | 0.3 | 0.11 | 36.7 |
| d,l-Amphetamine | 3.0 | 6.51 | 217.0 |
| | 1.0 | 1.48 | 148.0 |
| | 0.3 | 0.33 | 110.0 |
| | 0.15 | 0.12 | 80.0 |
| d-Methamphetamine | 8.0 | 6.39 | 79.9 |
| | 3.0 | 2.86 | 95.3 |
| | 1.0 | 1.07 | 107.0 |
| | 0.3 | 0.33 | 110.0 |
| | 0.15 | 0.17 | 113.3 |
| l-Methamphetamine | 8.0 | 0.41 | 5.1 |
| | 3.0 | 0.13 | 4.3 |
| d,l-Methamphetamine | 8.0 | 5.49 | 68.6 |
| | 3.0 | 2.21 | 73.7 |
| | 1.0 | 0.78 | 78.0 |
| | 0.3 | 0.23 | 76.7 |
| | 0.15 | 0.11 | 73.3 |
| 3,4-Methylenedioxy-amphetamine (MDA) | 3.0 | 5.31 | 177.0 |
| | 1.0 | 1.51 | 151.0 |
| | 0.3 | 0.45 | 150.0 |
| | 0.15 | 0.15 | 100.0 |
| 3,4-Methylenedioxy- | 8.0 | 2.75 | 34.4 |

TABLE 2-continued

| Test Compound | Concentration Added (ug/mL) | Concentration Found (ug/mL) | % Cross Re-activity |
|---|---|---|---|
| ethylamphetamine (MDE) | 3.0 | 1.22 | 40.7 |
| | 1.0 | 0.54 | 54.0 |
| | 0.3 | 0.21 | 70.0 |
| | 0.15 | 0.11 | 73.3 |
| 3,4-Methylenedioxy-methamphetamine (MDMA) | 3.0 | 3.06 | 102.0 |
| | 1.0 | 0.99 | 99.0 |
| | 0.3 | 0.30 | 100.0 |
| | 0.15 | 0.13 | 86.7 |
| 4-methyl-2,5-dimethoxy-amphetamine (DOM) | 100.0 | 2.41 | 2.4 |
| | 10.0 | 0.32 | 3.2 |
| | 8.0 | 0.28 | 3.5 |
| | 3.0 | 0.14 | 4.7 |
| 4-ethyl-2,5-dimethoxy amphetamine (DOET) | 100.0 | 1.91 | 1.9 |
| | 10.0 | 0.29 | 2.9 |
| | 8.0 | 0.27 | 3.4 |
| | 3.0 | 0.14 | 4.7 |
| p-Hydroxy-amphetamine | 10.0 | 3.09 | 30.9 |
| | 1.0 | 0.27 | 27.0 |
| 4-Chloroamphetamine | 5.0 | 6.12 | 122.4 |
| | 1.0 | 0.91 | 91.0 |
| | 0.3 | 0.22 | 73.3 |

As can be seen by an examination of the data presented in Table 3, the assay system of the present invention has minimal cross-reactivity to certain amphetamine-like compounds. Cross-reactivity was tested with compounds that have similar chemical structures to amphetamine and d-methamphetamine. Several amines which occur naturally in urine were tested as well. Representative data are shown in Table 3 below.

TABLE 3

| Test Compound | Concentration Added (ug/mL) | Concentration Found (ug/mL) | % Cross Re-activity |
|---|---|---|---|
| Fenfluramine | 50.0 | 7.37 | 14.7 |
| | 10.0 | 1.90 | 19.0 |
| | 1.0 | 0.20 | 20.0 |
| Isometheptene | 50.0 | 5.15 | 10.3 |
| | 10.0 | 1.02 | 10.2 |
| | 12.0 | 0.22 | 11.0 |
| Isoxsuprine | 100.0 | 0.90 | 0.9 |
| | 25.0 | 0.14 | 0.6 |
| Labetalol | 250.0 | 4.86 | 1.9 |
| | 100.0 | 0.90 | 0.9 |
| | 25.0 | 0.16 | 0.6 |
| Mephentermine | 100.0 | 5.28 | 5.3 |
| | 10.0 | 0.47 | 4.7 |
| Methoxypenamine | 100.0 | 2.40 | 2.4 |
| | 10.0 | 0.20 | 2.0 |
| 5-Methoxy-tryptamine | 100.0 | 0.85 | 0.9 |
| | 50.0 | 0.41 | 0.8 |
| | 25.0 | 0.19 | 0.8 |
| Nylidrin | 100.0 | 0.74 | 0.7 |
| | 25.0 | 0.10 | 0.4 |
| Phenethylamine | 100.0 | 0.25 | 0.3 |
| Phenmetrazine | 100.0 | 0.82 | 0.8 |
| Phentermine | 10.0 | 4.40 | 44.0 |
| | 1.0 | 0.35 | 35.0 |
| Propylhexedrine | 10.0 | 1.90 | 19.0 |
| | 1.0 | 0.34 | 34.0 |
| Tranylcypromine | 100.0 | 0.25 | 0.3 |
| Trimethobenzamide | 100.0 | 0.58 | 0.6 |
| | 50.0 | 0.35 | 0.7 |
| Tyramine | 100.0 | 0.45 | 0.5 |
| | 75.0 | 0.35 | 0.5 |
| | 50.0 | 0.20 | 0.4 |
| Tryptamine | 100.0 | 0.54 | 0.5 |
| | 50.0 | 0.21 | 0.4 |

The compounds shown in Table 4 yielded results less than the sensitivity of the assay (0.10 ug/mL) when tested up to the concentrations shown.

TABLE 4

| Compound Tested | Conc. Tested (ug/mL) |
|---|---|
| Acetaminophen | 100 |
| Acetanilide | 100 |
| Acetaphenazine | 100 |
| Acetazolamide | 100 |
| N-Acetyl-L-cysteine | 100 |
| Acetylsalicylic Acid | 100 |
| Allopurinol | 100 |
| Alpha-Methyl-L-Dopa | 100 |
| Alphaprodine | 100 |
| Alprazolam | 100 |
| Amantadine | 100 |
| Aminoglutethimide | 100 |
| Aminopyrine | 100 |
| Amitriptyline | 100 |
| cis-10-OH-Amitriptyline | 100 |
| trans-10-OH-Amitriptyline | 100 |
| Ammonium Chloride | 100 |
| Amobarbital | 100 |
| Amoxapine | 100 |
| Amoxicillin | 100 |
| Ampicillin | 100 |
| Anileridine | 100 |
| Aniline | 100 |
| Apomorphine | 10 |
| Aprobarbital | 100 |
| Ascorbic acid | 100 |
| Aspartame | 100 |
| Atenolol | 100 |
| Atropine | 100 |
| Barbital | 100 |
| Barbituric Acid | 100 |
| Bemegride | 100 |
| Benactyzine | 100 |
| Benzathine | 1000 |
| Benzocaine | 100 |
| Benzoic Acid | 100 |
| Benzoylecgonine | 100 |
| Benztropine | 100 |
| Bromocriptine Mesylate | 100 |
| Caffeine | 1000 |
| Calcium Hypochlorite | 100 |
| Carbamazepine | 100 |
| Carbamazepine-10-11-Epoxide | 100 |
| Carbamyl-B-methyl-Choline-Chloride | 100 |
| Carisoprodol | 100 |
| Carphenazine | 100 |
| Cephalexin | 100 |
| Cephaloridine | 100 |
| Cephradine | 100 |
| Chloramphenicol | 100 |
| Chlordiazepoxide | 100 |
| Chloroquine | 100 |
| Chlorothiazide | 100 |
| Chlorpheniramine | 100 |
| Chlorpromazine | 100 |
| Chlorpropamide | 100 |
| Chlorprothixene | 100 |
| Chlorthalidone | 100 |
| Cholesterol | 100 |
| Cimetidine | 1000 |
| Clindamycin | 100 |
| Clomipramine | 100 |
| Clonidine | 100 |
| Cocaine | 100 |
| Codeine | 100 |
| Cloxacillin | 100 |
| 1-Cortinine | 100 |
| Colchicine | 100 |
| Cortisone | 100 |
| B-Cortol | 100 |
| Cyclizine | 100 |
| Cyclobenzaprine | 100 |
| Cyclophosphamide | 100 |
| Cyproheptadine | 100 |

TABLE 4-continued

| Compound Tested | Conc. Tested (ug/mL) |
|---|---|
| Deoxycorticosterone | 100 |
| Desipramine | 100 |
| Dextromethorphan | 100 |
| Brompheniramine | 100 |
| Butabarbital | 100 |
| Butalbital | 100 |
| Butethal (Butobarbital) | 100 |
| Digitoxin | 100 |
| Digoxin | 100 |
| Dihydrocodeine | 100 |
| Dihydromorphine | 100 |
| Diphenhydramine | 100 |
| Diphenoxylate | 100 |
| Dipyridamole | 100 |
| Disopyramide | 100 |
| Disulfiram | 100 |
| L-Dopa | 100 |
| Dopamine | 100 |
| Dothiepin | 100 |
| Doxapram | 100 |
| Doxepin | 100 |
| Doxylamine | 100 |
| Ecgonine | 100 |
| EPPD (Methadone Metabolite) | 100 |
| Ephedrine | 3000 |
| d,l-Epinephrine | 1000 |
| Erythromycin | 100 |
| Estinyl | 10 |
| Estriol | 100 |
| Estrone | 100 |
| Estrone-3-sulfate | 100 |
| Ethambutol | 100 |
| Ethamivan | 100 |
| Ethinamate | 100 |
| Ethosuximide | 100 |
| Ethylmorphine | 100 |
| Fentanyl | 100 |
| Fluphenazine | 100 |
| Furosemide | 100 |
| Gentisic Acid | 100 |
| Glutethimide | 100 |
| Glycopyrrolate | 100 |
| Dicetylmorphine | 10 |
| Diazepam | 100 |
| Dibenzepin | 100 |
| Diflunisal | 100 |
| 5-Hydroxyphenyl-5-phenylhydantoin | 500 |
| Hydroxyzine | 100 |
| Ibuprofen | 500 |
| Imidazole-4-Acetic Acid | 100 |
| Imipramine | 100 |
| d,l-3-Indole Lactic Acid | 100 |
| Iproniazid | 100 |
| Isoproterenol | 100 |
| Kanamycin | 100 |
| Ketamine | 100 |
| Ketoprofen | 100 |
| Levallorphan | 100 |
| Levorphanol | 100 |
| Levothyroxine | 100 |
| Lidocaine | 100 |
| Lithium Carbonate | 100 |
| Loxapine | 100 |
| Maprotiline | 100 |
| Mazindol | 1000 |
| Mebendazole | 100 |
| Mefanamic Acid | 100 |
| MEGX | 100 |
| Melphalan | 100 |
| Meperidine | 100 |
| Mephenytoin | 100 |
| Meprobamate | 100 |
| Mescaline | 100 |
| d,l-Metanephrine | 100 |
| Metaproterenol | 100 |
| 6-Mercaptopurine | 100 |
| Methadone | 100 |
| Methaqualone | 100 |

TABLE 4-continued

| Compound Tested | Conc. Tested (ug/mL) |
|---|---|
| Methocarbamol | 100 |
| Methotrimeprazine | 100 |
| Grifulvin | 100 |
| Guaiacol Glyceryl Ether | 100 |
| Haloperidol | 100 |
| Hippuric Acid | 100 |
| Hydralazine | 100 |
| Hydrochlorothiazide | 100 |
| Hydrocodeine | 100 |
| Hydrocodone | 100 |
| Hydrocortisone | 100 |
| Hydromorphone | 100 |
| 5-Hydroxy Indole-3-Acetic Acid | 100 |
| Nalorphine | 100 |
| Naloxone | 100 |
| Naltrexone | 100 |
| Naproxen | 100 |
| Neomycin Sulfate | 100 |
| Niacinamide | 100 |
| Nicotine | 100 |
| Nicotinic Acid | 100 |
| Nifedipine | 100 |
| Nikethamide | 100 |
| p-Nitrophenol | 100 |
| Nomifensine | 100 |
| Norcodeine | 100 |
| Nordarvon | 100 |
| Norepinephrine | 1000 |
| Noresthisterone (Norethindrone) | 100 |
| Noroxymorphone | 100 |
| Nortriptyline | 100 |
| cis-10-OH-Nortriptyline | 100 |
| trans-10-OH-Nortriptyline | 100 |
| Noscapine | 100 |
| Octopamine | 1000 |
| Opipramol | 100 |
| Orotic Acid | 100 |
| Orphenadrine | 100 |
| Oxazepam | 100 |
| 3-Methoxytyramine | 100 |
| Methoxypromazine | 100 |
| Methsuximide | 100 |
| Methyprylon | 100 |
| Metoprolol | 100 |
| Mianserin | 100 |
| 6-Monoacetylmorphine | 100 |
| Morphine | 100 |
| Morphine-B-3-D-glucuronide | 100 |
| Nadolol | 100 |
| Phenacetin | 100 |
| Phenelzine | 100 |
| Phenformin | 100 |
| Pheniramine | 100 |
| Phenobarbital | 100 |
| Phenothiazine | 100 |
| Phenylacetone | 100 |
| d,1-Phenylalanine | 100 |
| Phenylbutazone | 100 |
| Phenylephrine | 100 |
| Phenylpropanolamine | 1000 |
| Phenytoin | 100 |
| Picotoxin | 100 |
| Piperacetazine | 100 |
| Piroxicam | 100 |
| Potassium Chloride | 100 |
| Potassium Iodide | 100 |
| Prazosin | 100 |
| Prednisolone | 100 |
| Prednisone | 100 |
| Pregnenolone | 10 |
| Primidone | 100 |
| Probenecid | 100 |
| Procainamide | 100 |
| Procaine | 100 |
| Prochlorperazine | 100 |
| Progesterone | 10 |
| Oxycodone | 100 |
| Oxymetazoline | 100 |
| Oxymorphone | 100 |
| Oxyphenbutazone | 100 |
| Papaverine | 100 |
| Paramethasone | 100 |
| Pargyline | 100 |
| Pemoline | 100 |
| Penicillin | 100 |
| Pentazocine | 100 |
| Pentobarbital | 100 |
| Perphenazine | 100 |
| Phencyclidine | 100 |
| Phendimetrazine | 100 |
| 1-Phenyl Cyclohexylamine | 100 |
| 4-OH-Piperidine-Phencyclidine | 100 |
| 1-Piperidine Cyclohexane | 100 |
| Secobarbital | 100 |
| Serotonin | 100 |
| Strychnine | 100 |
| Sudoxicam | 100 |
| Sulfamethazine | 100 |
| Sulfathiazole | 100 |
| Sufisoxazole | 100 |
| Sulindac | 100 |
| Talbutal | 100 |
| Terbutaline | 100 |
| Testosterone | 100 |
| Tetracycline | 100 |
| Tetrahydrozoline | 100 |
| -9-Tetrahydro-cannabinol-9-carboxylic acid | 10 |
| Thebaine | 100 |
| Theophylline | 100 |
| Thiamine | 100 |
| Thiopropazate | 100 |
| Thioridazine | 100 |
| Thiothixene | 100 |
| Promazine | 100 |
| Promethazine | 100 |
| proplomazine | 100 |
| Propoxyphene | 100 |
| Propranolol | 100 |
| (+)Pseudoephedrine | 3000 |
| (−)Pseudoephedrine | 3000 |
| Protriptyline | 100 |
| Pyridoxine | 100 |
| Pyrilamine | 100 |
| Quinidine | 100 |
| Quinine | 100 |
| Rauwolfia serpentina Indian | 10 |
| Reserphine | 100 |
| Salbutamol | 100 |
| Salicylate | 1000 |
| Scopolamine | 100 |
| Tolbutamide | 100 |
| Trazodone | 100 |
| Triamcinolone | 100 |
| Triamterene | 100 |
| Triethylperazine | 100 |
| Trifluoperazine | 100 |
| Triflupromazine | 100 |
| Trihexyphenidyl | 100 |
| Trimethadione | 100 |
| Trimethoprim | 100 |
| Trimipramine | 100 |
| Tripelennamine | 100 |
| Triprolidine | 100 |
| Tryptophan | 100 |
| Tyrosine | 100 |
| Uric Acid | 100 |
| Urea | 100 |
| Verapamil | 100 |
| Warfarin | 100 |
| Zomepirac | 100 |

Carryover was determined by assaying a d-amphetamine solution in normal human urine at 350 ug/mL followed by a sample of drug-free normal human urine. Percent Carryover = 100× (measured concentration of amphetamine found in the drug-free urine divided by the concentration of the d-amphetamine solution). Percent Carryover was determined to be less than or equal to 0.02%.

The amphetamine/methamphetamine assay, in accordance with the analytical methods of the preferred embodiment of the present invention, involves pretreating a urine sample containing or suspected of containing amphetamine and/or d-methamphetamine with an effective amount of an aqueous periodate solution having a pH from about 4 to 7.5 for a period of time sufficient to eliminate undesired cross-reactivity. Preferably, the sample is pretreated with 0.1 to 0.25 molar aqueous sodium periodate solution for about 1 to 9 minutes, most preferably 4 to 5 minutes at a temperature range from about 31° to about 36° C.

The pretreated sample is then mixed with tracer and antibody reagents specific to amphetamine and to d-methamphetamine. Amphetamine or d-methamphetamine and the tracers compete for limited antibody sites, resulting in the formation of antibody-ligand complexes. By maintaining a constant concentration of tracer and antibody, the ratio of antibody drug complex to tracer-antibody complex formed upon incubation is directly proportional to the amount of amphetamine and/or d-methamphetamine in the sample. Therefore, upon exciting the mixture with plane polarized light and measuring the polarization of the fluorescence emitted by a tracer and a tracer-antibody complex, one is able quantitatively or qualitatively to determine the amount of amphetamine and/or d-methamphetamine in the sample.

The results can be quantified in terms of net millipolarization units, span (in millipolarization units) and relative intensity. The measurement of millipolarization units indicates the maximum polarization when a maximum amount of the tracer is bound to the antibody in the absence of amphetamine or d-methamphetamine. The amount of tracer bound to the antibody is directly proportional to the net millipolarizaiton. For purposes of the present invention, a net millipolarization value of over 190 is ideal, but a value in the range of about 150 to about 220 is acceptable. The span is an indication of the difference between the net millipolarization at the points of the maximum and the minimum amount of tracer bound to the antibody. A larger span provides for a better quantitative analysis of data. For the purposes of this invention, a span of at least about 60 millipolarization units is preferred. The intensity is a measure of the amplitude of the fluorescence signal that is above the background fluorescence. Thus, a higher intensity will give a more accurate measurement. The intensity is determined for the preferred tracers of the invention as the sum of the vertically polarized intensity plus twice the horizontally polarized intensity. The intensity can range from a signal of about three times to about thirty times the background noise depending upon the concentration of the tracer and other assay variables. For the purposes of the present invention, an intensity of at least eight to ten times that of noise background is preferred.

Table 5 shows the results obtained with the preferred antibodies raised in response to immunogens and tracer compounds of the present invention in terms of span and millipolarization units. As seen from the data in Table 5, an assay using the antibody produced from the immunogen of Structure 20 in combination with the tracer of Structure 1 provides excellent results for an amphetamine assay. For assay of d-methamphetamine, a combination of antisera derived from an immunogen of Structure 21 with tracer of FIG. 7 provides excellent results.

One aspect of the present assay that is unique is the combination of antisera produced from immunogens of Structure 20 and Structure 21 with tracers of Structure 1 and Structure 7 to produce an assay with a net polarization of 213 mP and a span over 73 mP for either amphetamine or methamphetamine. This is the most preferred configuration of the assay.

TABLE 5

| Hapten Used In Immunogen For Antibody | Tracer | Sample Volume | Net Polarization | Span |
|---|---|---|---|---|
| Structure 20 | Structure 1 | 4 uL | 252.11 | 119.11 |
| Structure 20 | Structure 1 | 6 uL | 253.84 | 136.48 |
| Structure 20 | Structure 2 | 6 uL | 227.77 | 103.68 |
| Structure 20 | Structure 4 | 10 uL | 152.48 | 77.80 |
| Structure 21 | Structure 7 | 6 uL | 215.33 | 110.12 |
| Structures 20 & Structure 21 | Structures 1 & Structure 7 | 8 uL | 213.09 | 73.87 |

The pH at which the method of the present invention is conducted must be sufficient to allow the fluorescein moiety of the tracers to exist in their open form. The pH may range from about 3 to 12, more usually in the range of from about 5 to 10, most preferably from about 6 to 8. Various buffers may be used to achieve and maintain the pH during the assay procedure. Representative buffers include borate, phosphate, carbonate, tris, barbital and the like. The particular buffer employed is not critical to the present invention, but phosphate buffer is preferred. The cation portion of the buffer will generally determine the cation portion of the tracer salt in solution.

The preferred-method of the improved assay of the present invention is discussed in detail in Example 5. The assay is a "homogenous assay," which means that the end polarization readings are taken from a solution in which bound tracer is not separated from unbound tracer. This is a distinct advantage over heterogeneous immunoassay procedures where the bound tracer must be separated from the unbound tracer.

As described previously herein, the reagents for the fluorescence polarization assay of the present invention comprise antibodies specific for amphetamine and d-methamphetamine in a solution containing riboflavin binding protein, fluorescein tracer analogs of amphetamine and d-methamphetamine and a periodate pretreatment solution. Additionally, conventional amphetamine/d-methamphetamine assay solutions, including a dilution buffer, d-amphetamine calibrators and d-amphetamine controls are preferably prepared.

The preferred procedure is especially designed to be used in conjunction with the ABBOTT LABORATORIES' TD$_x$® Clinical Analyzer and the ABBOTT LABORATORIES' AD$_x$® Abused Drug System, both of which are available from Abbott Laboratories, Irving, Tx. It is to be understood that when either the ABBOTT LABORATORIES' TD$_x$® Clinical Analyzer or the ABBOTT LABORATORIES' AD$_x$® Abused Drug System is used, the assay is fully automated from pretreatment to final reading. However, manual assay can be performed. In the case of automated and manual assays, the sample is mixed with the pretreatment solution in dilution buffer and a background reading is taken. The tracer is then mixed with the assay. The antibody is then finally mixed into the test solution. After incubation, a fluorescence polarization reading is taken and processed. In the case of both manual and automated assays, the present method eliminates the need for sample pH adjustment.

The following examples describe and illustrate the present invention in greater detail. Both an explanation of, and the actual procedure for, the various aspects of the invention are described where appropriate.

EXAMPLE 1

Preparation of Amphetamine Tracers

3-(2-nitro-1-propen-1-yl)benzoic acid

Preferred Amphetamine Tracer

To a solution of 1.902 q (12.68 mmol) of 3-carboxybenzaldehyde in 10 mL of glacial acetic acid, was added 2.848 mL (2.970 g, 38.04mmol) of nitroethane and 1.080 g (13.95 mmol) of ammonium acetate. The solution was then heated with stirring under nitrogen in a 110° C. oil bath. Then, all of the solid went into solution near 60° C. and the mixture turned a deep yellow color. After 3 hours, thin layer chromatography with 3:1 hexane/EtOAc indicated that no starting material remained. The reaction mixture was cooled to room temperature, and then partitioned between water and methylene chloride, with acidification to about pH2 with 6 M HCl. The organic layer was washed with 6 M HCl, then dried with magnesium sulfate. The solvents were then removed with a rotary evaporator, yielding 2.768 g (98%) of crude material, which was carried on without further purification because of the difficulty of chromatographing the very polar carboxylic acid.

3-(2-nitro-1-propenyl)benzoic acid-methyl ester

A solution of 2.768g of 3 (2-nitro 1-propenyl)benzoic acid in 30 mL of boron trifluoridemethanol complex was heated at reflux with stirring under nitrogen for 2 hours, then allowed to come to room temperature with stirring overnight. Preparative thin layer chromatography with 3:1 hexane/etOAc indicated that no starting material remained. The mixture was partitioned between methylene chloride and 5% sodium bicarbonate. (Caution was necessary because of foaming.) The organic layer was dried over magnesium sulfate, and solvents were removed with a rotary evaporator, yielding 2.40 g of crude ester. The crude product was purified on a 40×2.5 cm flash silica column, eluted with 4:1 hexane/EtOAc yielding 1.036 g (37%) of the title compound as a pale yellow crystalline solid.

3-(2-aminopropyl)benzyl alcohol

In an oven-dried flask under nitrogen atmosphere was placed 12.15 mL (12.15 mmol) of 1.0 M borane in THF. This was chilled in an ice bath. A solution of 596 mg (2.7 mmol) of 3 (2 nitro 1 propenyl)benzoic acid-methyl ester in 10 mL dry THF was added to the stirred solution via syringe. Solid sodium borohydride (51.3 mg, 1.35 mmol) was then added to the mixture quickly. The mixture was stirred in the ice bath an additional 5 minutes, then at room temperature for 15 minutes The yellow color faded to colorless after about 5 minutes at room temperature. The solution was then heated at a gentle reflux under nitrogen overnight. The reaction mixture was cooled to room temperature and quenched by dropwise addition of 500 mL of water, then reheated at a gentle reflux for 2 hours. The reaction mixture was again cooled to room temperature and filtered and the residue was washed with water. The combined filtrate and washings were then basified to pH 14 with KOH pellets. Methylene chloride was used to extract the product, with the extraction being repeated 3 times (3x5ml). The solution was dried with sodium sulfate, and volatile materials were removed with a rotary evaporator. The crude amine weighed 273 mg (57%). It was carried on without purification.

3-(2-trifluoroacetamidopropyl)benzyl alcohol

To a solution of 254 mg (1.44 mmol) of 3-(2-amino propyl)benzyl alcohol in 4 mL meOH was added 254 uL (302 mg, 2.13 mmol) of ethyl trifluoroacetate and 220 uL (1.57 mmol) of triethylamine (7.17 M). The solution was then stirred at ambient temperature overnight. Thin layer chromatography with chloroform-/MeOH indicated that no starting material was present. The solution was then partitioned between 6M HCl and EtOAc, and the organic layer was dried (sodium sulfate), and concentrated on a rotary evaporator, yielding 321 mg (86%) of the protected amino alcohol.

3-(2-trifluoroacetamidocropyl)benzoic acid

To a solution of 321 mg (1.23 mmol) of 3-(2-trifluoroacetamidopropyl)benzyl alcohol in 4 mL acetone was added 55 uL (1.48 mmol) of Jones' Reagent (2.7 M). When thin layer chromatography with hexane/EtOAc after 45 minutes showed some of the intermediate aldehyde remaining, 55 uL more of Jones' Reagent was added. Thin layer chromatography after 30 additional minutes showed one spot. Three drops of isopropanol were added to the reaction mixture to consume excess chromium (VI), and it was allowed to stir 30 minutes more. The reaction mixture was then diluted with an equal volume of methylene chloride and filtered through a small amount of silica gel. Volatile materials were removed on a rotary evaporator, yielding 224 mg (66%) of the benzoic acid as an off-white solid.

6-[3-(2-trifluoroacetamidoprop-1-yl) benzamido]fluorescein

Method A: Using oxalyl chloride

Dichloroethane (1 mL) was added to 37 mg (0.1345 mmol) of 3 (2 trifluoroacetamidoprop-1-yl)benzoic acid in a 5 mL flask (not very soluble). 16.5 uL (0.188 mmol, 1.4 eq) of oxalyl chloride was added, followed by 0.5 uL of DMF. The flask was sealed with a septum and gas evolution was monitored by means of a bubbler which was connected through a syringe needle. The mixture was stirred at room temperature, swirling the flask occasionally to get solid off the sides. Two small additional portions of oxalyl chloride were added when gas evolution had ceased before all starting material had dissolved. When all solid had finally dissolved and gas evolution had ceased (approximately 2 to 3 hours), the solvent was blown off under a nitrogen stream, leaving a solid, approximately the same color as the starting acid. Fluoresceinamine Isomer II (37 mg, 0.107 mmol, 0.8 eq) was added, along with 1 mL of dry acetonitrile, and the mixture was stirred, capped with a septum overnight 14 hr) at room temperature. Examination by thin layer chromatography (chloroform/MeOH) revealed that most of the fluoresceinamine had been consumed. The mixture was diluted with a little MeOH to bring everything into solution and streaked onto two 20×20cm×1 mm silica plates, which were developed twice with chloroform/MeOH. Elution of the major product band produced 41 mg of red solid after careful removal of solvent. A second chromatography on four 20×20cm×0.5 mm silica plates, again developed with chloroform/MeOH (1:1:1 benzene/EtOAc/acetone may be used instead) gave 35 mg containing only a trace of higher Rf material. A third chromatography on four 20×20cm×0.5 mm plates as above gave 28 mg of protected tracer which has deprotected as below.

Method B: Using isobutyl carbonate mixed anhydride

A 9.6 mg sample of 3-(2-trifluoroacetamidoprop-1-yl) benzoic acid (0.035 mmol) was dissolved in 0.30 mL of dry acetonitrile (Aldrich Gold Label), chilled in an ice/water bath and treated with 5.4 uL of triethylamine (0.0385 mmol, 1.1 eq) and 5.0 uL of isobutyl chloroformate (0.0385 mmol, 1.1 eq). The mixture was stirred capped for ½ hr in the ice bath, then ½ hr at room temperature. Solid fluoresceinamine isomer II (10.4 mg, 0.03 mmol, 0.86 eq) was added, and the mixture was stirred at room temperature overnight. Examinations by thin layer chromatography appeared to reveal a better yield of the desired product after 2 hours than after 23 hours. Hydrolysis was carried out with 100 uL of methanol, 25 uL of water and 25 uL of concentrated aqueous ammonia for 2 and ½ hours, and the product was purified by chromatographing three times on silica, twice with 5:1 chloroform/methanol, and once with 1:1:1 benzene/ethyl acetate/acetone.

Method C1: Using BOP-Cl

A solution of 104 mg (0.38 mmol) of 3-(2-trifluoroacetamidoprop-1-yl)benzoic acid in 3.0 mL acetonitrile was stirred with 53 uL (0.38 mmol) triethylamine (7.17 M), 114 mg (.33 mmol) of fluoresceinamine isomer II and 97 mg (0.38 mmol) of bis(2-oxo-3-oxazolidinyl)- phosphinic chloride (BOP-Cl) at room temperature overnight. (The BOP-Cl was added last). Preparative thin layer chromatography with 1:1:1 benzene/EtOAc/acetone showed unreacted fluoresceinamine; however, the addition of more BOP-Cl did not seem to affect the reaction. 1.0 mL of MeOH, 250 uL water, and 250 uL ammonia were than added for hydrolysis of 0-acylated fluorescein derivatives. After stirring 1 hour, the volatile materials were removed under a nitrogen stream. The residue was then redissolved in MeOH and stripped under nitrogen 2 times. The material was then streaked onto two 20×20cm×2 mm silica gel plates and developed two times with 1:1:1 benzene/EtOAc/acetone. (The material would have benefitted from another chromatography on thinner plates, i.e.: 0.5 mm plates).

Method C2: Using BOP Cl

A 27.5 mg sample of 3-(2-trifluoroacetamidoprop-1-yl)benzoic acid (0.1 mmol) was taken up in 1.0 mL of dry acetonitrile (Aldrich Gold Label) (not all dissolves) and treated with 6.9 uL of pyridine (0.085 mmol, 0.85 eq) and 25.5 mg of BOP-Cl (0.1 mmol, 1.0 eq), stirring at room temperature for 15 minutes. The fluoresceinamine isomer II (29.5 mg, 0.085 mmol, 0.85 eq) was then added, and stirring was continued overnight at room temperature with exclusion of moisture. Workup and chromatography was as above, scaled appropriately.

6-[3-(2-aminopropyl)benzamido]fluorescein

The entire sample of the protected tracer from the experiment described under Method C1 was deprotected overnight by stirring with 1600 uL MeOH and 800 uL potassium carbonate (1.0M aqueous). After 24 hours, preparative thin layer chromatography showed almost no protected tracer remaining. The reaction mixture was then streaked onto four 20×20cm×0.5 mm silica gel plates and developed two times with 1:1 chloroform/MeOH +2% ammonia. The plates were somewhat streaky, so the chromatography procedure was repeated.

17.8 mg (.0343 mmol) of the tracer was obtained by removing the solvents. The material was redissolved into 4 mL MeOH and reacted with 10 uL triethylamine and 9.3 mg (0.0428 mmol) of di-tert-butyl dicarbonate (BOC) overnight at room temperature. Preparative thin layer chromatography showed no polar material remaining. Solvents were removed under nitrogen, and the reaction mixture was redissolved in a small volume of methanol and streaked onto two 20×20cm×0.5 mm silica gel plates. The plates were developed two times with 5:1 chloroform/MeOH. The second major band from the top of the plates was scraped and eluted with mathanol. The material was concentrated to dryness and redissolved in 2.0 mL of trifluoroacetic acid. Preparative thin layer chromatography in 5:1 chloroform/MeOH after 35 minutes showed no starting material remaining. The solvent/reagent was removed under nitrogen, and the residue redissolved in MeOH and blown down under nitrogen two times to remove most of the residual trifluoroacetic acid.

(R,S)-5-[2-Trifluoroacetylamido-1-propyl
(phen-3-ylaminocarbo-nyl)]fluorescein and
(R,S)-6-[2-trifluoroacetylamido-1-propyl
(phen-3-ylaminocarbonyl)]fluorescein A mixture of 5- and 6- carboxylfluorescein (9.4 mg) was dissolved in 0.125 mL of dimethylformamide and chilled in an ice bath. Triethylamine (0.0115 mL) and isobutyl chloroformate (0.0107 mL) were added, and the mixture was allowed to stire for 2 hours as the ice melted. A solution of (R,S)-3-(2-trifluoroacetamido-prop-1-yl) aminobenzene (6.6 mg) in another 0.125 mL of dimethylformamide was added, and stirring was continued at room temperature overnight. The mixture was diluted with 0.125 mL of methanol and 0.020 mL of water and treated with 0.020 mL of concentrated aqueous ammonia. After stirring for a further 3 hours, volatile materials were removed under a stream of nitrogen. The residue was purified by chromatography on a thin layer plate with chloroform/methanol to give (R,S) 5-[2-trifluoroacetyl-amido-1-propyl (phen-3 ylaminocarbonyl)]-fluorescein and (R,S)-6-[2-trifluoroacetylamido-1-propyl (phen-3-ylaminocarbo nyl)]fluorescein as the two major products.

(R,S)-5-[2-Amino-1
propyl(phen-3-ylaninocarbonyl)]fluorescein

The (R,S)-5-[2-trifluoroacetylamido-1-propyl(phen-3-ylaminocarbonyl)]fluorescein produced in the preceding example was dissolved in 0.5 mL of methanol and treated with 0.2 mL of a 1.0 M solution of potassium carbonate. The mixture was stirred at ambient temperature for 15 hours. Chromatography on a thin layer plate with chloroform/methanol/ammonia produced the pure title compound.

(R,S)-6-[2-Amino-1-propyl(phen-3-ylaminocarbonyl)]-fluorescein

This compound was prepared by hydrolysis of (R,S)-6-[2-trifluoroacetylamido-1-propyl(phen-3-ylaminocarbonyl)]-fluorescein exactly as in the preceding example.

(R,S)-2-(2-Trifluoroacetamidoprop-1-yl-)aminobenzene

Neat (R,S)-1-phenyl-2-propanol (6.18 g, 50 mmol) was slowly added dropwise to 35 mL of ice-chilled trifluoroacetic anhydride. The mixture was stirred for 15 minutes after completion of the addition, still in the ice bath. Concentrated nitric acid (3.21 mL, 51 mmol) was then added dropwise, and the mixture was stirred for a further 45 minutes with ice cooling. Volatile materials were removed on a rotary, evaporator, and the residue was partitioned between 3% sodium bicarbonate and dichloromethane. The organic phase was dried over anhydrous magnesium sulfate, filtered and concentrated to leave 13.29 g of a pale yellow oil which showed NMR signals appropriate for a mixture of mostly 4-nitro , some 2-nitro- and a little 3-nitrophenyl-2-propyl trifluoroacetate.

A 2.2 g sample of the mixed nitro isomers produced in the preceding reaction was hydrolysed by dissolving in 10 mL of methanol and 10 mL of 1M aqueous sodium hydroxide. The mixture, which was initially two phases, became homogeneous after stirring overnight at ambient temperature. The reaction was quenched after 18 hours by neutralizing with 3M aqueous hydrochloric acid, and most of the methanol was removed on a rotary evaporator. The aqueous residue was extracted with dichloromethane, and the organic layer was washed once with water. Drying over anhydrous magnesium sulfate, filtration, and removal of solvent left 1.3 g of yellow oil (96.5%). The isomers were separated by flash chromatography on a silica gel column with hexane/ethyl acetate, with the (R,S)-1-(2-nitrophenyl)-2-propanol eluting first.

A solution of 265 mg of (R,S)-1-(2-nitrophenyl)2-propanol (1.46 mmol) in 6 mL of dichloromethane was chilled in an ice bath and treated with 0.286 ml (2.05 mmol) of triethylamine, followed by 210 mg (1.83 mmol) of methanesulfonyl chloride. The mixture was stirred for 2 hours while it gradually warmed to room temperature. The product was isolated by extraction with water and then with 5% sodium bicarbonate, drying over anhydrous magnesium sulfate, filtration and removal of solvent to give a near-quantitative yield of quite pure (R,S)-1-(2-nitrophenyl)-2-propyl methanesulfonate as a yellowish-tan solid.

A portion of the methanesulfonate ester produced in the preceding reaction (348 mg, 1.34 mmol) was dissolved in 4 mL of dimethylformamide. Sodium azide (175 mg, 2.68 mmol) was added, and the mixture was stirred in an oil bath at 115° for 1½ hours. After cooling to room temperature, products were isolated by partitioning between ether and water, drying over anhydrous magnesium sulfate, filtration and removal of solvent. The clear yellowish oil which remained (263 mg) was about 75% (R,S)-1-(2 nitrophenyl)-2-azidopropane by NMR, with the remainder consisting mostly of a mixture of elimination products. Since these compounds did not separate well on chromatography, the mixture was carried on without purification.

A portion (230 mg) of the impure azide produced in the preceding reaction was reduced by dissolving in 3 mL of tetrahydrofuran and treating with triphenylphosphine (322 mg). After gas evolution commenced, 30 mg water was added to hydrolyse the intermediate, and the mixture was heated in 45° oil bath under a nitrogen atmosphere overnight. After 15 hours it was cooled to room temperature and volatile materials were removed. The residue was dissolved in 10 mL of dichloromethane and 0.30 mL of trifluoroacetic anhydride was added. After 1 hour the solvent was removed to leave 750 mg of a golden oil which was flash chromatographed to give 184 mg of (R,S)-1-(2-nitrophenyl)-2-trifluoroacetamidopropane as a white crystalline solid.

A portion (131 mg) of the nitro compound produced in the preceding reaction was dissolved in 15 mL of ethyl acetate and hydrogenated over 25 mg of 10% palladium on carbon on a Parr shaker to give a near-quantitative yield of (R,S)-2-(2-trifluoroacetamidoprop-1-yl)aminobenzene as a clear colorless oil.

(R,S)-5-[2-Trifluoroacetylamido-1-propyl (phen-2-ylaminocarbonyl)]fluorescein and (R,S)-6-[2-trifluoroacetylamido-1-propyl (phen-2-ylaminocarbonyl)]fluorescein These compounds were prepared from 6.6 mg of (R,S)-2-(2-trifluoro acetamidoprop-1-yl)aminobenzene according to the method of the immediately preceding Example.

(R,S)-5-[2-Amino-1-propyl(phen-2-ylaminocarbonyl)]-fluorescein

This compound was prepared from (R,S) 5-[2-trifluoroacetylamido-1-propyl (phen-2-ylaminocarbonyl)]fluorescein according to the method of the immediately preceding Example.

(R,S)-6-[2-Amino-1-propyl(phen-2-ylaminocarbonyl)]-fluorescein

This compound was prepared from (R,S)-6-[2-trifluoroacetylamido-1-propyl (phen-2-ylaminocarbonyl)]fluorescein according to the method of the Example immediately preceding the immediately preceding Example.

(R,S)-5-[3-(2-Trifluoroacetamidoprop-1-yl)-benzamido]fluorescein

Dichloroethane 0.4 mL) was added to 11.0 mg (0.04 mmol) of 3-2-trifluoroacetamidoprop-1-yl)benzoic acid in a small vial (not all of the solid dissolved initially), and 7.1 mg of oxalyl chloride was added with good stirring. No change was visible until a small amount (ca. 0.001 mL) of dimethylformamide was added. This produced vigorous gas evolution. After stirring at room temperature for 3 hours, the solution was divided into two equal portions, and one was blown down to dryness under a stream of nitrogen. Solid 5-aminofluorescein (5.6 mg, 0.016 mmol) was added, followed by 0.1 mL of dimethylformamide, and the resulting mixture was stirred at ambient temperature for 17 hours. The solvent was removed under a stream of nitrogen, and the residue was chromatographed on a silica gel thin layer plate with chloroform/methanol to give the title compound.

(R,S)-5-[3-(2-Aminoprop-1-yl) benzamido]fluorescein

One half of the sample of (R,S)-5-[3-(2-trifluoroacetamidoprop-1-yl) benzamido]fluorescein prepared in the preceding example was dissolved in 0.4 mL of methanol and hydrolysed by treatment with 0.2 mL of 1 M aqueous potassium carbonate, stirring at ambient temperature overnight. The product was purified by chromatography on a silica gel thin layer plate with chloroform/methanol/ammonia.

EXAMPLE 2

Preparation of d-Methamphetamine Tracer (1R2S)-1-Phenyl-1-hydroxy-2-[trifluoroacetyl(methyl)amido]propane Preferred d Methamphetamine Tracer To a solution of 13.55 g (82.00 mmol) of (1R2S)-(−)-ephedrine in 75 mL of methanol stirring under nitrogen in an ice water bath, was added 12.23 mL (14.55 g, 102.5 mmol) of ethyl trifluoroacetate and 11.71 mL (90.2 mmol) of thriethylamine. The solution was stirred in the ice bath for two hours and then at room temperature for two hours. Preparative thin layer chromatography with 5:1 hexane/EtOAc indicated that no starting material was remaining. The reaction mixture was partitioned between 6M HCl and ethyl acetate. The organic layer was then dried with sodium sulfate and concentrated on a rotary evaporator to yield 14.943 g (70%) of the protected ephedrine as a colorless oil. The compound did not require any purification.

(S)-1-Phenyl-2-[trifluoroacetyl(methyl)amido]propane

A solution of 13.28 g (50.1 mmol) of (1R2S) 1-phenyl-1-hydroxy 2-[trifluoroacetyl(methyl)amido]propane in 55 mL of THF with 7.33 mL (51.9 mmol) of trifluoroacetic anhydride was shaken on a hydrogenerator with 1.4 g of 10% palladium on carbon. After 3 days, the pressure dropped 23 psi. The reaction mixture was then filtered through diatomaceous earth and concentrated on a rotary evaporator. A preparative thin layer chromatography with 3:1 hexane/EtOAc indicated that some starting material was still present. The reaction mixture was then redissolved in 55 mL THF and shaken 24 additional hours with another 7.33 mL of trifluoroacetic anhydride and 1.4 g of 10% palladium on carbon catalyst. The pressure dropped 27 psi. The reaction mixture was again filtered and concentrated on a rotary evaporator. The preparative thin layer chromatography and $^1$HNMR showed no starting material present. The reaction produced 10.928 g (89%) of the title compound as a colorless oil, which was carried on without further purification.

(S)-1-(2 Nitrophenyl)-2-[trifluoroacety(methyl)amido]propane,
(S)-1-(3-Nitrophenyl)-2[trifluoroacety(methyl)amido]propane, and
(S)-1-(4-Nitrophenyl)-2-[trifluoroacety(methyl)amido]propane To a solution of 2.297 g (9.3-8 mmol) of (S)-1-phenyl-2-[trifluoroacetyl(methyl)amido]propane in 8 mL of trifluoroacetic anhydride stirring in a ice water bath was added 615 uL (9.56 mmol) of 70% nitric acid (15.55 M) over a period of 10 minutes. The reaction was then allowed to continue stirring in the ice bath for three hours. The reaction mixture was blown to dryness under a nitrogen stream and the residue was partitioned between methylene chloride and 5% aqueous sodium bicarbonate. (Caution was necessary because of foaming.) The organic layer was then dried over sodium sulfate and concentrated to dryness yielding 1.39 g of crude material, which was purified on a flash silica gel column using a mixture of hexane/ethyl acetate as the mobile phase. The 2-nitro- was the most mobile, and the 4-nitro- was the least mobile of the three isomers produced. The chromatography isolated 260 mg of pure (S)-1-(2-nitrophenyl)-2-[trifluoroacetyl(methyl)amido]propane and 512 mg of pure (S)-1-(4-nitrophenyl)-2-[trifluoroacetyl(methyl)amido]propane, with much material coming off the column in mixed fractions. Combining some of the middle fractions gave 60 mg of impure (S)-1-(3-nitrophenyl)-2-[trifluoroacetyl-(methyl)amido]propane, which was further purified by rechromatographing on thin layer plates with hexane/ethyl acetate to give 34 mg of pure material.

(S)-1-(4-Aminophenyl)-2-[trifluoroacetyl(methyl)amido]propane

A solution of 107 mg of (S)-1-(4-nitrophenyl)2-[trifluoroacetyl(methyl)amido]propane in 10 mL of ethanol was shaken on a hydrogenerator with 11 mg of palladium on carbon. After 1 hour, the pressure had dropped 6 psi and the reaction mixture was taken off and filtered through diatomaceous earth. The resulting solution was then concentrated to dryness yielding 73 mg of the title compound as a near-colorless oil.

(S)-6-[2-trifluoroacetyl(methyl)amido 1-propyl (4-pheny aminocarbonyl)]fluorescein A solution of 73 mg (0.280 mmol) of (S)-1-(4-aminophenyl) 2-[trifluoroacetyl(methyl)amido]propane in 2.0 mL of dry acetonitrile was stirred with 84 mg (0.224 mmol) of 6-carboxy fluorescein and 39 uL (280 mmol) of triethylamine and 107 mg (0.420 mmol) of bis(2-oxo-3-oxazolidinyl)phosphinic chloride (BOP-Cl) at room temperature for three days. (The BOP-Cl was added last. The reaction probably would have been complete after 16–18 hours of stirring.) Preparative thin layer chromatography with 5:1 chloroform/methanol indicated about a 40% conversion to protected tracer, and since not much higher Rf material was observed, no hydrolysis was indicated. The reaction mixture was diluted with an equal volume of methanol and streaked onto two 20×20 cm×2 mm silica el plates which were developed four times with 5:1 chloroform/methanol. The main tracer band from each plate was then scraped and eluted with methanol and rechromatographed on four 20×20 cm×0.55 mm silica gel plates developed two times with 5:1 chloroform/methanol.

(S)-6-(2-methylaminoprop-1-ylphen-4-ylaminocarbonyl)fluorescein

The entire sample of the protected tracer from the previous experiment was deprotected overnight by stirring in 2.0 mL of methanol with 1.0 mL of 1M aqueous potassium carbonate. After 24 hours, analytical thin layer chromatography showed almost no protected tracer remaining. The reaction mixture was streaked onto four 20×20 cm×0.5 mm silica gel plates, which were developed two times with 1:1 chloroform/methanol+2% ammonia. Elution with methanol gave a solution of the title compound.

(S)-1-(2-nitrophenyl)-2-[trifluoroacetyl(methyl) amido]propane and
(S)-1-(4-nitrophenyl)-2-[trifluoroace tyle(methyl)amido]propane To a solution of 2.297 g (9.38 mmol) of (S)-1-phenyl-2-[trifluoroacetyl(methyl)amido]propane in 8 ml of trifluoroacetic anhydride stirring in an ice-water bath was added 0.615 mL (9.56 mmol) of 70% nitric acid over a period of 10 minutes. The reaction was then allowed to continue stirring in the ice bath for 3 hours. The reaction mixture was blown to dryness under a nitrogen steam, and the residue was partitioned between methylene chloride and 5% aqueous sodium bicarbonate. The organic layer was then dried over sodium sulfate and concentrated to dryness, yielding 1.39 g of crude material, which was purified on a flash silica gel column using hexane/EtOAc as the mobile phase. The 2-nitro- was the most mobile, and the 4-nitro- was the least mobile of the three isomers produced. The chromatography isolated 260k mg of pure S)-1-(2-nitrophenyl)-2-[trifluoroacetyl(methyl)amido]propane and 512 mg of pure (S)-1-(4-nitrophenyl)-2-[trifluoro-acetyl(methyl)amido]propane, with much material coming off the column in mixed fractions.

(S)-1-(2-Aminophenyl)-2-[trifluoroacetyl(methyl)amido]propane (S)-1-(2-Nitrophenyl)-2-[trifluoroacetyl(methyl)amido]propane (247 mg) was dissolved in 10 mL of ethanol and hydrogenated over 25 mg of 10% palladium on charcoal on a Parr shaker. After 1½ hours, filtration and removal of solvent left 220 mg of a colorless glass.

(S)-5-[2-(2-Trifluoroacetyl(methyl)amido-1-propyl)phenyl-aminocarbonyl]fluorescein and (S)-6-[2-(2 trifluoroacetyle (methyl)amino-1-propyl)phenylaminocarbonyl]fluorescein A solution of a 10.0 mg of carboxyfluorescein (Kodak, mixed 5- and 6-isomers) in 0.13 mL of dimethylformamide was chilled in an ice-water bath and treated with 12 mg of isobutyl chloroformate and 0.0122 mL of trithylamine. The solution was stirred for 1¾ hours, warming slowly to room temperature. (S)-1-(2-nitrophenyl)-2-[trifluoroacetyl(methyl) amido]propane (7.6 mg) was added as a solution in another 0.13 mL of dimethylformamide, and the mixture was stirred at ambient temperature for 17 hours. The mixture was diluted with 0.13 mL of methanol and 0.03 mL of water, and hydrolysed 0.03 mL of concentrated aqueous ammonia, stirring at room temperature for 2 hours. Volatile materials were removed under a nitrogen stream, and the products were isolated by chromatography on a thin layer silica gel plate developed with chloroform/methanol.

(S)-5-[2-Methylamino-1-propyl)phenylaminocarbonyl]-fluorescein

One half of the sample of (S)-5-[2-(2-trifluoroacetyl(-methyl)amido-1-propyl)phenylaminocarbonyl]fluorescein was hydrolysed by dissolving in 0.4 mL of methanol and treating with 0.2 mL of 1M aqueous potassium carbonate, stirring at ambient temperature for 16 hours. Chromatography on a thin layer silica gel plate developed with chloroform/methanol/ammonia gave the pure product.

(S)-6-[2-(2-Methylamino-1 propyl)phenylaminocarbonyl]fluorescein

This compound was prepared from (S)-6-[2-(2-trifluoroacetyl(methyl)amino-1-propyl)phenylaminocarbonyl]fluorescein exactly as in the immediately preceding Example.

(S)-6-[4-(2-Methylamino-1-propyl)phenylaminocarbonyl]fluorescein

This compound was prepared in two steps from 10 mg of (S)-1-(4-nitrophenyl)-2-[trifluoroacetyl(methyl)amido]propane in the manner described hereinabove.

EXAMPLE 3

Preparation of Amphetamine Immunogens

1-(3-Nitrophenyl)-2-nitropropene

Preferred Amphetamine Immunogen

A mixture of 7.56 g (50 mmol) of 3-nitrobenzaldehyde, 11.25 g (150 mmol) of nitroethane and 4.24 g (55 mmol) of ammonium acetate was heated in 2 mL of acetic acid in a 110° C. oil bath for 2 1/2 hours. Subsequent examination of the mixture by preparative thin layer chromatography with hexane/ethyl acetate showed almost no starting material remaining. Volatile materials were removed with a rotary evaporator, and the residue was partitioned between dichloromethane and water, with washing of the organic layer twice with 10% sodium bicarbonate. Caution was necessary because gas evolution occurred during the first bicarbonate wash. Drying was performed with magnesium sulfate. Filtration and removal of solvent left 9.13 g of crude product. Half of this was chromatographed on a 3×35 cm flash silica column, packed with hexane and eluted with 7:1 hexane/ethyl acetate to give 1.66 g (32%) of pure title compound.

(R,S)-3-(2-Trifluoroacetamidoprop-1-yl)nitrobenzene

Twenty-four milliliters of 1.0 M borane-THF (14 mmol) was transferred into a dry 100 mL flask chilled in an ice/water bath under a nitrogen atmosphere. A solution of 1.66 g of 1-(3-nitrophenyl)-2-nitropropene in 22 mL of dry THF was added, followed by 151 mg (4 mmol) of solid sodium borohydride. A significant amount of gas evolution occurred, and the yellow color of the solution disappeared within 5 minutes. The ice bath was removed and the flask was allowed to come to room temperature for 15 minutes. It was then heated in a 70° C. oil bath for 8 hours. (More than 8 hours of heating in a 70° C. oil bath may be necessary for maximum yield.) The reaction was quenched by careful, dropwise addition of 1.4 mL of water. Then, the mixture was heated with stirring in the 70° oil bath for an additional 1 hour. Solvents were removed from the mixture with a rotary evaporator, and the residue was partitioned between 0.5 M aqueous sodium hydroxide and dichloromethane. The residue was then dried with magnesium sulfate. Filtration and removal of solvent left 1.48 g of crude (R,S)-3-(2-aminopropyl) nitrobenzene, which was protected as follows before purification.

The entire sample of crude (R,S)-3-(2-aminopropyl)-nitrobenzene was dissolved in 15 mL of methanol, treated with 1.39 mL (10 mmol) of triethylamine and 1.28 g (1.01 mL, 10 mmol, 1.25 eq) of methyl trifluoroacetate, and stirred at room temperature for 2 and ½ days (longer than necessary). Removal of solvent and excess reagents left 2.74 g of residue, which was chromatographed on a flash silica column, packed with hexane and eluted with hexane/ethyl acetate. The yield of pure (R,S)-3-(2-trifluoroacetamidoprop-1-yl) nitrobenzene was 1.022 g (47%). It had a melting point of 141°-142° C. after recrystallization from hexane ethyl acetate. The NMR spectrum at 200 MHz in a mixture of deuterochloroform and deuteromethanol showed signals at 1.3 (doublet, 3H), 2.95 (complex multiplet, 2H), 4.3 (complex multiplet, 1H), 7.6 (multiplet, 2H) and 8.1 ppm (multiplet, 2H).

(R,S)-3-(2-Trifluoroacetamidoprop-1-yl)aminobenzene

A solution of 152 mg of 3-(2-trifluoroacetamidoprop-1-yl) nitrobenzene in 10 mL of ethyl acetate was shaken on a Parr shaker at room temperature with 20 mg of 10% palladium on charcoal at an initial overpressure of 35 psi. A pressure drop of 5 psi occurred within 30 minutes, and the reaction was removed from the shaker after 1 hour and fifteen minutes. The catalyst was removed by filtration through a pad of diatomaceous earth, and the solvent was removed, leaving a quantitative yield of the title compound as a clear colorless oil. It showed NMR signals at 200 MHz in deuterochloroform of 1.2 (doublet, 3HO), 2.8 (complex multiplet, 2H), 4.2 (complex multiplet, 1H), 6.2 (broad singlet, 1H), 6.6 several multiplets, 3H) and 7.1 ppm (apparent triplet, 1H).

d,l -Amphetamine Immunogen (R,S)-3-(2-Trifluoroacetamidoprop-1-yl) aminobenzene (48 mg, 0.195 mmol) was diazotized in 3 mL of water and 2 mL of acetone at 0° by treatment with 14.8 mg (0.214 mmol) of sodium nitrite and 0.158 mL of 3M aqueous hydrochloric acid. After stirring for 15 minutes, this mixture was added to a well-stirred solution of 200 mg of bovine thyroglobulin in 12 mL of 2M sodium hydroxide, also chilled in an ice bath. Removal of the protecting group was carried out by continuing the stirring overnight at room temperature under a nitrogen atmosphere. The solution was then dialyzed against 0.1 M sodium chloride at 2° to 8° C.

EXAMPLE 4

Preparation of Methamphetamine Immunogens (S)-1-(4-Chlorosulfonylphenyl)-2-[trifluoroacetyl (methyl)amido]propane Neat chlorosulfonic acid (1.5 mL) was added to 164 mg of (S)-1-phenyl-2-[trifluoroacetyl(methyl)amido]propane in a small flask. The solution was stirred at ambient temperature for 15 minutes, and then was heated in a 40° bath for 1.5 hours. It was cooled to room temperature, diluted with 40 ml of dichloromethane and poured into a mixture of ice and saturated aqueous sodium chloride in a separatory funnel. The organic phase was dried over anhydrous magnesium sulfate and filtered through a small bed of silicagel. Removal of solvent left 175 mg of a nearly colorless glass, which showed NMR resonances in deuterochloroform at 1.3 (two doublets) for the terminal methyl, 2.0 (two singlets and a multiplet) for the N-methyl and benzylic methylene, 4.3 and 4.9 (a smaller and a larger multiplet) for the methine, and 7.45 (two doublets) and 7.95 ppm (two doublets) for the para disubstituted aromatic.

d-Methamphetamine Sulfonamide Immunogen

Bovine thyroqlobulin (390 mg) was dissolved in 19.5 mL of 0.1 M disodium phosphate and 3.9 mL of dimethylformamide was added. A solution of 39 mg of (S)-1-(4-chlorosulfonylphenyl)-2-[trifluoroacetyl(methyl)amido]propane in 3.9 mL of dimethylformamide was then stirred in, with stirring being continued at ambient temperature overnight. The pH of the solution was adjusted to 13 with 10M sodium hydroxide, and the reaction was stirred for a further 16 hours to hydrolyze off the trifluoroacetyl protecting group. The material was dialysed against distilled water.

2-Position Azo-d-methamphetamine Immunogen

A solution of 247 mg of (S)-1-(2-nitrophenyl)-2-[trifluoroacetyl (methyl)amido]propane in 10 mL of ethanol was hydrogenated over 25 mg of 10% palladium on charcoal on a Parr shaker to give 220 mg of (S)-1-(2-aminophenyl)-2-[trifluoroacetyl(methyl)amido]propane as a colorless glass.

A solution of 107 mg of the above amine plus 31 mg of sodium nitrite in 3 mL of water and 0.5 mL of acetone was chilled in an ice bath and treated with 0.3 mL of 3 M aqueous hydrochloric acid. This mixture was stirred in the cold for 15 minutes and then added dropwise to a well-stirred solution of 200 mg of bovine thyroglobulin in 20 mL of water and 2 mL of 10 M aqueous sodium hydroxide, also chilled in an ice bath. After stirring for 15 minutes, the solution was placed under a nitrogen atmosphere, capped and stirred in a cold room overnight to complete removal of the protecting group. The pH was adjusted to 7, and it was dialyzed against 0.1 M saline in a cold room.

3-Position Azo-d-methamphetamine Immunogen

A 30 mg sample of (S)-1-(3-aminophenyl)-2-[trifluoroacetyl(methyl)amido]propane was prepared from 34 mg of (S)-1-(3-nitrophenyl)-2-[trifluoroacetyl(methyl)amido]propane as in the first part of the immediately preceding Example (2-Position Azo-d-methamphetamine Immunogen). The immunogen was prepared from 29 mg of this material and 120 mg of bovine thyroqlobulin, as in the second part of the immediately preceding Example.

4-Position Azo-d-methamphetamine Immunogen

This immunogen was prepared from 99.4 mg of (S)-1-(4-aminophenyl)-2-[trifluoro acetyl(methyl)amido]propane and 200 mg of bovine thyroqlobulin, as in the second part of the immediately preceding Example (3-Position Azo-d-methamphetamine Immunogen).

EXAMPLE 5

Amphetamine/Methamphetamine Assay

A. Reagents
  (1) Pretreatment Solution—A solution containing about 0.20 sodium periodate (pH 4.5).
  (2) Tracer: Consisting of the preferred tracer prepared in Example 3 (FIG. 17) and the preferred tracer prepared in Example 4 (FIG. 18). Each compound is in 0.1 M sodium phosphate buffer at pH 7.5 containing 0.01% w/v bovine gamma globulin, and 0.1% w/v sodium azide.
  (3) Antibody: Rabbit or sheep antiserum consisting of antiserum raised against amphetamine and d-methamphetamine appropriately diluted in 0.1 M sodium phosphate buffer, 0.1% sodium azide, 2% propylene glycol and 15 mg/mL riboflavin binding protein.
  (4) Diluent buffer: 0.1 M sodium phosphate, pH 7.5, 0.01% bovine gamma globulin and 0.1% sodium azide.
  (5) Calibrators: pooled normal human urine preserved with 0.1% sodium azide having d-amphetamine levels as follows: 0.00, 0.15, 0.30, 1.0, 3.0, and 8.0 ug/mL.
(6) Controls: pooled normal human urine preserved with 0.1% sodium azide, containing 0.5, 1.50 or 4.0 ug/mL of d-amphetamine.
(7) Wash: A solution containing about 5% propylene glycol in 0.45% NaCl.

All polarized fluorescence measurements were made using the ABBOTT LABORATORIES' TD$_x$ ® Clinical Analyzer.

B. Assay Protocol
(1) Equal portions of an unknown sample and pretreatment solution are pipetted into the predilute well. A sufficient volume of diluent buffer is added to raise the volume to 500 ul. This mixture is incubated for 4-6 minutes.
(2) A sample from the predilute well and 25 ul of antibody is pipetted into the cuvette. A background intensity reading is taken.
(3) 25 ul each of tracer and antibody, and a sample from the predilute well, is added to the cuvette. Sufficient diluent buffer is added to raise the final volume to 2.0 mLs.
(4) The fluorescence polarization due to tracer binding to the antibody is obtained by substracting the polarized fluorescence intensities of the background from the final polarized fluorescence intensities of the mixture.
(5) The polarization values obtained are inversely proportional to the amphetamine and/or methamphetamine concentration of each sample.
(6) The polarization value for a sample is compared to a standard curve prepared using calibrators of known amphetamine or d-methamphetamine content.

EXAMPLE 6

Sodium Periodate Pretreatment

Samples containing 100 and 1000 ug/mL of phenylpropanolamine were assayed with the ABBOTT LABORATORIES' TD$_x$ ® Clinical Analyzer with and without the preincubation treatment described in Example 5B above. The assay utilized the combined amphetamine/d-methamphetamine tracers of Structures 1 and 7 and the antibodies produced by the immunogens of FIGS. 20 and 21. Results are presented in Table 6 below:

TABLE 6

| ug/mL Phenylpropanolamine | Response Equivalent to |
| --- | --- |
| 100 without pretreatment | 1.39 ug/mL Amphetamine |
| 1000 with pretreatment | <0.1 ug/mL Amphetamine |

The above results illustrate that sodium periodate treatment of samples without the addition of pH raising constituents, such as base, is effective in eliminating β-hydroxyphenethylamine cross-reactivity and is useful for such purpose in amphetamine/methamphetamine fluorescence polarization assays.

While the present invention has been described herein with some particularity, those of skill in the art will recognize numerous modifications and variations which remain within the spirit of the invention. These modifications and variations are within the scope of the invention as described and claimed herein.

What is claimed is:

1. A method for detecting the presence, or determining the amount, of amphetamine and/or d-methamphetamine in a test sample of biological fluid by fluorescence polarization assay comprising the steps of:
(a) intermixing the test sample with:
(1) a salt of a first tracer of Formula 1

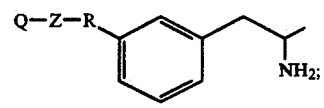

(2) a salt of a second tracer of Formula 3

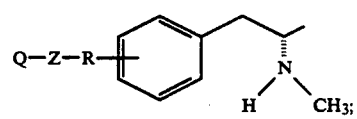

wherein for each of Formula 1 and Formula 3
Q is fluorescein or a derivative of fluorescein,
Z is >NH, >C=O or >SO$_2$, and
R is a linking group including up to 5 heteroatoms and having a total of from 0 to 15 carbon atoms and heteroatoms,
(3) a first antibody capable of specifically recognizing and binding amphetamine or the first tracer; and
(4) a second antibody capable of specifically recognizing and binding d-methamphetamine or the second tracer; and
(b) determining the amounts of tracers bound to the first or second antibodies by fluorescence polarization techniques as a measure of the amount of amphetamine and d-methamphetamine in the sample.

2. The method according to claim 1 wherein:
(a) the first antibody has been raised against a compound of Formula 7

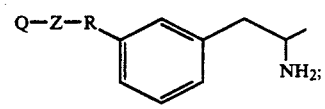

(b) the second antibody has been raised against a compound of Formula 9

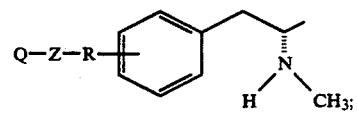

wherein for each of Formula 7 and Formula 9,
Q is an immunogenic carrier,
Z is >NH, >C=O or >SO$_2$, and
R is a linking group including up to 5 heteroatoms and having a total of from 0 to 5 carbon atoms and heteroatoms.

3. The method according to claim 1 wherein:
(a) the first tracer is

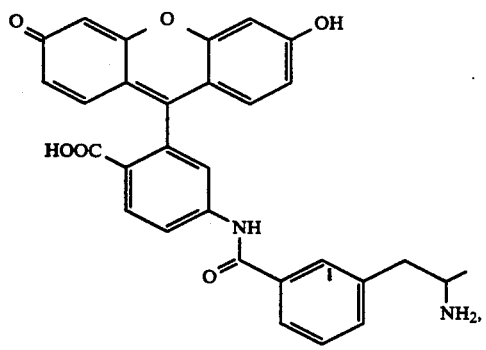
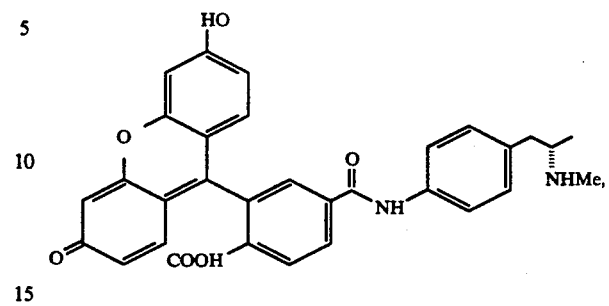
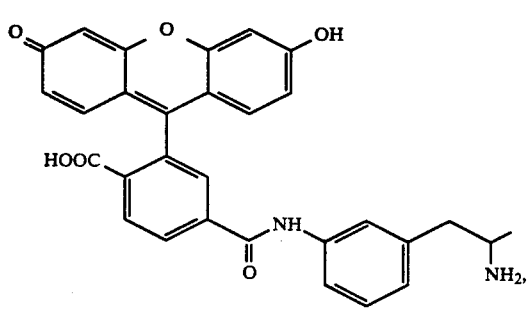
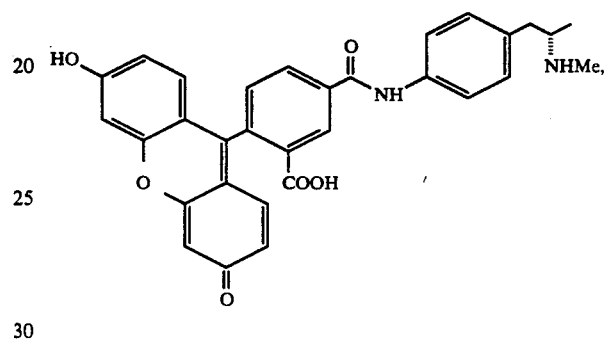
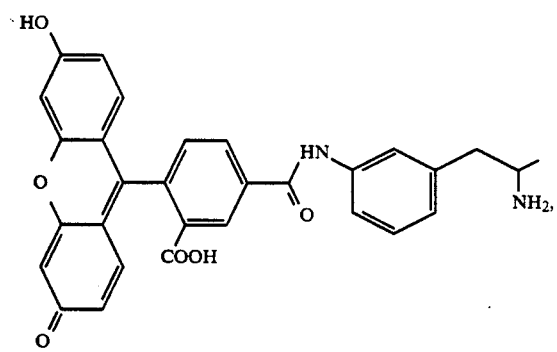
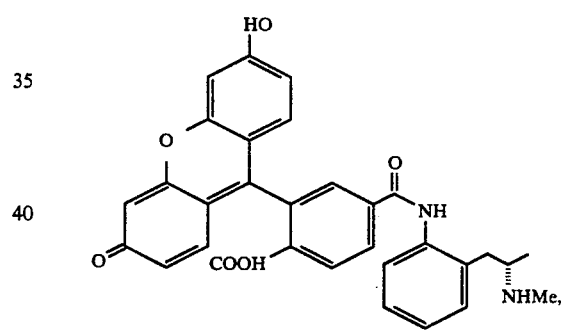
or
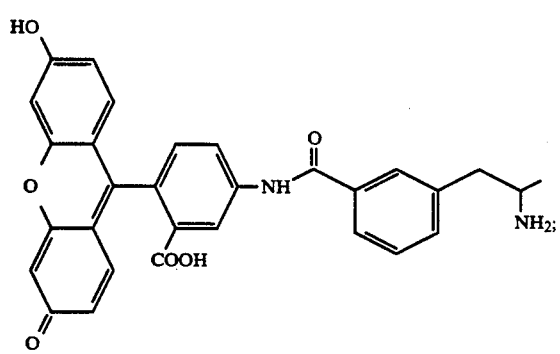
and
(b) said second tracer is
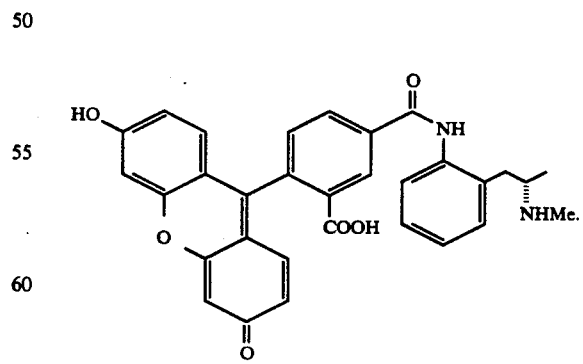
or
4. The method according to claim 3 wherein the first tracer is

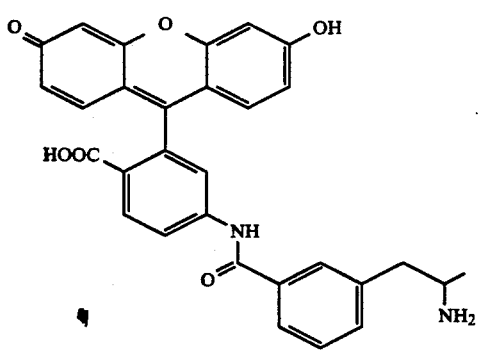

and the second tracer is

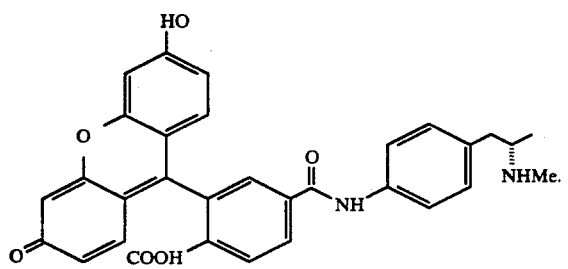

5. The method according to claim 2 wherein:
(a) the first antibody has been raised against an immunogen which has the structure

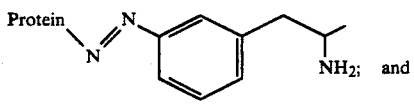 and (b) the second antibody has been raised against an immunogen which has the structure

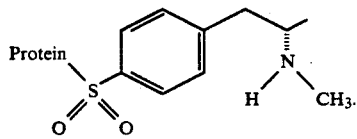

6. The method according to claim 3 wherein:
(a) the first antibody has been raised against an immunogen which has the structure

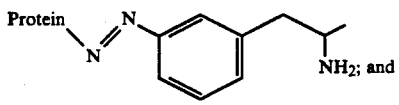 and (b) said second antibody has been raised against an immunogen which has the structure

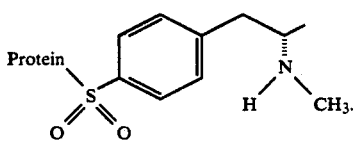

7. The method according to claim 4 wherein:
(a) the first antibody has been raised against an immunogen which has the structure

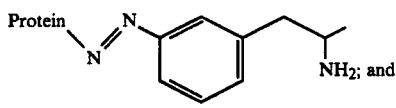 and (b) the second antibody has been raised against an immunogen which has the structure

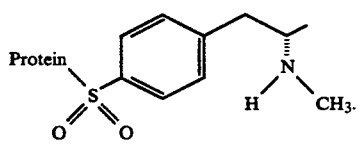

8. The method according to claim 1 wherein Q is fluorescein.

9. The method according to claim 1 wherein an amount of riboflavin binding protein which is effective to reduce fluorescence interference by riboflavin is added to the sample.

10. A reagent kit useful in the determination of amphetamine and d-methamphetamine in biological samples comprising:
(a) a salt of a first tracer of Formula 1

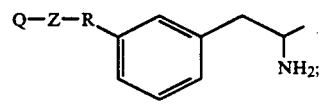

(b) a salt of a second tracer of Formula 3

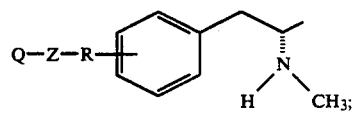

wherein for each of Formula 1 and Formula 3
Q is fluorescein or a derivative of fluorescein,
Z is $>$NH, $>$C$=$O or $>$SO$_2$, and
R is a linking group including up to 5 heteroatoms and having a total of from 0 to 15 carbon atoms and heteroatoms, (c) a first antibody capable of specifically recognizing and binding amphetamine or the first tracer; and (d) a second antibody capable of specifically recognizing and binding d-methamphetamine or the second tracer.

11. The reagent kit according to claim 10 wherein:
(a) the first antibody has been raised against a compound of Formula 7

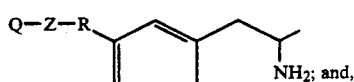

(b) the second antibody has been raised against a compound of Formula 9

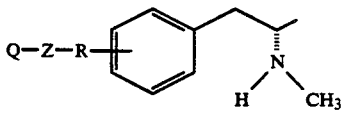

wherein for each of Formula 7 and Formula 9,
Q is an immunogenic carrier,
Z is >NH, >C=O or >SO$_2$, and
R is a linking group including up to 5 heteroatoms and having a total of from 0 to 15 carbon atoms and heteroatoms.

12. The reagent kit according to claim 10 which further comprises an aqueous pretreatment solution having an amount of periodate which is effective in the elimination of undesirable cross-reactivity to β-hydroxyphenethylamines.

13. The reagent kit according to claim 11 which further comprises an aqueous pretreatment solution having an amount of periodate which is effective in the elimination of undesirable cross-reactivity to β-hydroxyphenethylamines.

14. The reagent kit according to claim 10 which further comprises an amount of riboflavin binding protein which is effective to reduce fluorescence interference by riboflavin is added to the sample.

15. The reagent kit according to claim 11 which further comprises an amount of riboflavin binding protein which is effective to reduce fluorescence interference by riboflavin is added to the sample.

16. The reagent kit according to claim 12 which further comprises an amount of riboflavin binding protein which is effective to reduce fluorescence interference by riboflavin is added to the sample.

17. The reagent kit according to claim 13 which further comprises an amount of riboflavin binding protein which is effective to reduce fluorescence interference by riboflavin is added to the sample.

* * * * *